United States Patent

Tsuji et al.

[11] Patent Number: 5,976,515
[45] Date of Patent: *Nov. 2, 1999

[54] BLOOD FLOW AMOUNT-IMPROVING AGENT COMPRISING STEROID DERIVATIVE AND COSMETIC USING SAME

[75] Inventors: Kuniro Tsuji, Shizuoka; Junichi Shibata, Kanagawa; Masanori Okada, Kanagawa; Yasunori Inaoka, Kanagawa, all of Japan

[73] Assignees: Pola Chemical Industries, Inc., Kanagawa; Kuniro Tsuji, Shizuoka, both of Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/682,555
[22] PCT Filed: Dec. 9, 1994
[86] PCT No.: PCT/JP94/02075
§ 371 Date: Oct. 21, 1996
§ 102(e) Date: Oct. 21, 1996
[87] PCT Pub. No.: WO95/19160
PCT Pub. Date: Jul. 20, 1995

[30] Foreign Application Priority Data

Jan. 12, 1994 [JP] Japan .......................................... 6/1783
Jan. 12, 1994 [JP] Japan .......................................... 6/1785

[51] Int. Cl.$^6$ ..................................................... A61K 7/06
[52] U.S. Cl. .......................... 424/70.1; 424/401; 514/880; 514/881
[58] Field of Search ................................... 424/401, 70.1; 514/880, 881

[56] References Cited

U.S. PATENT DOCUMENTS 5,198,225  3/1993  Meybeck et al. ........................ 424/450

FOREIGN PATENT DOCUMENTS

90/03778     4/1990  WIPO .
WO 90/03778  4/1990  WIPO .
WO 93/12761  7/1993  WIPO .
WO 94/04132  3/1994  WIPO .

OTHER PUBLICATIONS

Inaoka et al., *Chemical Abstracts,* vol. 123, #122840, 1994.
Ohsawa et al . Studies on constituents of fruit body of Polyporous umbellatus and their cytotoxic activity. Chem. Pharm. Bull. vol. 40 (1), pp. 143–147, 1992.

*Primary Examiner*—Thurman K. Page
*Assistant Examiner*—Lakshmi Channavajjala
*Attorney, Agent, or Firm*—Knobbe, Martens, Olson & Bear, LLP

[57] ABSTRACT

A steroid derivative is used as a blood flow amount-improving agent, which is blended with a cosmetic preferably in a ratio of 0.000001 to 10% by weight with respect to a total amount of the cosmetic.

3 Claims, No Drawings

BLOOD FLOW AMOUNT-IMPROVING AGENT COMPRISING STEROID DERIVATIVE AND COSMETIC USING SAME

This application is a 371 of PCT/JP94/02075 filed on Dec. 9, 1994.

TECHNICAL FIELD

The present invention relates to a blood flow amount-improving agent, and to cosmetics containing it. In particular, the present invention relates to a blood flow amount-improving agent comprising a steroid derivative, and to cosmetics containing it, the cosmetics including, for example, a cosmetic for hair which is excellent in hair-growing effect, and a cosmetic for skin which is excellent in skin-beautifying effect.

BACKGROUND ART

Many people hope to permanently maintain plentiful, natural, and beautiful hairs on heads, regardless of young or old, or men or women. However, people suffer a lot of stresses in the modern society, such as social stresses and stresses concerning personal relationships. Such stresses badly affect hairs on heads, resulting in rapid increase, year by year, in the number of people who suffer from troubles concerning hairs on heads, such as alopecia. In response to such a situation, hair-growing agents have been hitherto developed, including, for example, extracts from galenicals such as *Coicis semen*, ginkgo, and ginger; vitamin E; alloxazine; and adenosine-3',5'-cyclic monophosphate (c-AMP). Any of these pharmaceuticals is known to have a function to improve the blood flow amount in minute peripheral blood vessels. It is considered that their hair-growing effects also result from such a function.

Among the hair-growing agents having the function as described above, the extracts from galenicals such as *Coicis semen*, ginkgo, and ginger are also known to have an effect on skin to improve a dermal state by improving the blood flow amount as well.

As described above, it is known for the cosmetic that the improvement in blood flow amount in minute peripheral blood vessels results in preferred effects such that the hair growth is facilitated on skin of head, and the dermal state is improved on skin of body.

However, any of the hair-growing agents described above is not fully sufficient in the hair-growing function. In addition, some of them are not preferable from a viewpoint of safety since adverse side effects such as dermatitis are caused as in the case of so-called 101 which brought about a boom. In general, no hair-growing agent capable of being put to practical use without any problem has been obtained until now. The skin cosmetics also have had their insufficient functions, being not suitable for practical use if they are evaluated also from the viewpoint of safety.

Thus it has been desired to develop a blood flow amount-improving agent which has an excellent function to improve the blood flow amount and has high safety, in order to obtain a cosmetic for hair which is excellent in the hair-growing effect, and a cosmetic for skin which is excellent in the function to improve the dermal state.

On the other hand, it has not been known that steroid derivatives as represented by general formulae (1) and (2) described below have the function to improve the blood flow amount. In addition, it has not been reported that they are blended with a cosmetic for hair or a cosmetic for skin so that the hair growth is facilitated, or the dermal state is improved.

DISCLOSURE OF THE INVENTION

The present invention has been made taking the viewpoints described above into consideration, an object of which is to provide a blood flow amount-improving agent which has an excellent blood flow amount-improving function and has high safety, and cosmetics containing it such as a cosmetic for hair which is excellent in the hair-growing effect, and a cosmetic for skin which is excellent in the skin-beautifying effect.

As a result of extensive and repeated screening for various pharmaceuticals and chemicals by the present inventors in order to achieve the object described above, it has been found that steroid derivatives represented by the following general formula (1) or (2) not only have high safety but also have an excellent blood flow amount-improving function. Thus the present invention has been completed.

Namely, the present invention lies in a blood flow amount-improving agent comprising a steroid derivative represented by the following general formula (1) or (2), and cosmetics containing it:

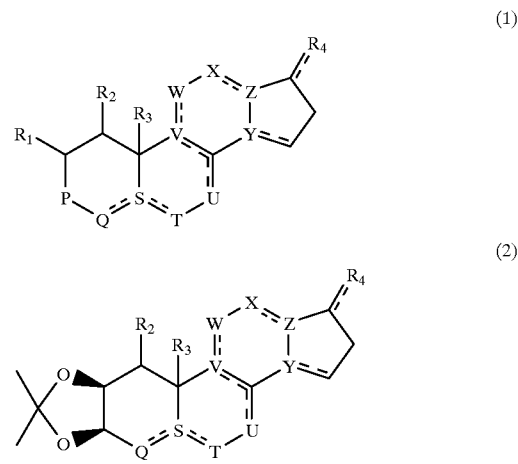

In the formulae, $R_1$, $R_2$, and $R_3$ independently represent hydrogen atom, hydroxyl group, short chain length alkyl group, short chain length alkyloxy group, short chain length acyl group, aromatic acyl group, short chain length acyloxy group, aromatic acyloxy group, or short chain length hydroxyalkyl group respectively.

Q, S, T, U, V, W, X, Y, and Z represent methine group, methylene group, or carbonyl group, optionally hydrogen atom being independently substituted with hydroxyl group or short chain length alkyl group respectively in the case of the methine group and the methylene group.

P represents methylene group or carbonyl group, optionally hydrogen atom being independently substituted with hydroxyl group, short chain length alkyl group, short chain length alkyloxy group, short chain length acyl group, aromatic acyl group, short chain length acyloxy group, aromatic acyloxy group, short chain length hydroxyalkyl group, or sugar residue respectively in the case of the methylene group.

$R_4$ represents oxygen atom, linear or branched alkyl group, alkenyl group, or acyl group having a number of carbon(s) of 1 to 12 in its carbon backbone, optionally hydrogen atom bound to carbon atom being independently substituted with hydroxyl group or carboxyl group respectively in the case of the groups other than the oxygen atom, optionally the hydroxyl group and the carboxyl group forming cyclic ether or lactone ring through intermolecular bond, optionally the hydroxyl group binding to short chain length carboxylic acid, aromatic carboxylic acid, or sulfuric acid through ester bond, or to sugar, lower alcohol, or glycol through ether bond, and optionally they forming salt.

In the present invention, the "short chain length" with respect to the short chain length alkyl group and the short chain length acyl group and so on, which is used in the definition in relation to the formula (1) or (2) described above, refers to the fact that the number of carbon(s) in the concerning group is 1 to 4.

The present invention will be described in detail below.

(1) Blood flow amount-improving agent of the present invention

The blood flow amount-improving agent of the present invention comprises the steroid derivative represented by the general formula (1) or (2) described above. In preferred embodiments, the steroid derivative represented by the general formula (1) or (2) used in the present invention specifically includes, for example, steroid derivatives shown in Table 1. Structural formulae of these steroid derivatives are shown in the following structural formulae (3) to (119) respectively. These steroid derivatives are assigned to Steroid Numbers as shown in Table 1. These Steroid Numbers will be hereinafter used in this specification when these steroid derivatives are referred to, if necessary.

TABLE 1

List of Steroid Derivatives Used as Blood Flow
Amount-Improving Agent of the Present Invention

| Name of compound | Structural formula | Steroid No. |
| --- | --- | --- |
| Paristerone | (3) | 1 |
| Ponasterone A | (4) | 2 |
| Ponasterone B | (5) | 3 |
| Ponasterone C | (6) | 4 |
| Inokosterone | (7) | 5 |
| Takisterone | (8) | 6 |
| Makisterone A | (9) | 7 |
| Makisterone B | (10) | 8 |
| Makisterone C | (11) | 9 |
| Makisterone D | (12) | 10 |
| Pterosterone | (13) | 11 |
| Stachysterone C | (14) | 12 |
| Stachysterone D | (15) | 13 |
| Viticosterone E | (16) | 14 |
| Sidasterone A | (17) | 15 |
| Sidasterone B | (18) | 16 |
| Ajugasterone B | (19) | 17 |
| Ajugasterone C | (20) | 18 |
| Amarasterone A | (21) | 19 |
| Amarasterone B | (22) | 20 |
| Cyasterone | (23) | 21 |
| Isocyasterone | (24) | 22 |
| Epicyasterone | (25) | 23 |
| Capitasterone | (26) | 24 |
| Precyasterone | (27) | 25 |
| Sengosterone | (28) | 26 |
| 26-Hydroxypolypodine B | (29) | 27 |
| 2-Deoxyecdysone | (30) | 28 |
| 3-Deoxyecdysone | (31) | 29 |
| 3-Dehydro-20-hydroxyecdysone | (32) | 30 |
| 3-Epiecdysone | (33) | 31 |
| 3-Epi-20-hydroxyecdysone | (34) | 32 |
| Kaladasterone | (35) | 33 |
| Podecdysone B | (36) | 34 |
| Calonysterone | (37) | 35 |
| Abutasterone | (38) | 36 |
| Ajugalactone | (39) | 37 |
| Ajugasterone D | (40) | 38 |
| Carpesterol | (41) | 39 |
| Carthamosterone | (42) | 40 |
| Cheilanthone A | (43) | 41 |
| Cheilanthone B | (44) | 42 |
| Cyasterone-22-acetate | (45) | 43 |
| Dacrysterone | (46) | 44 |
| 24(28)-Dehydromakisterone A | (47) | 45 |
| 5-Deoxykaladasterone | (48) | 46 |
| Deoxyviperidone | (49) | 47 |
| 24-Epimakisterone A | (50) | 48 |
| Integristerone A-22-O-α-D-galactopyranoside | (51) | 49 |
| Integristerone | (52) | 50 |
| 29-Norcyasterone | (53) | 51 |
| 29-Norcyasterone-2-acetate | (54) | 52 |
| 29-Norcyasterone-3-acetate | (55) | 53 |
| 29-Norsengosterone | (56) | 54 |

TABLE 1-continued

List of Steroid Derivatives Used as Blood Flow
Amount-Improving Agent of the Present Invention

| | | |
|---|---|---|
| Osladin | (57) | 55 |
| Pinnasterol | (58) | 56 |
| 14α-Hydroxypinnasterol | (59) | 57 |
| Pinnasterol-2-acetate | (60) | 58 |
| 14α-Hydroxypinnasterol-2-acetate | (61) | 59 |
| 14α-Hydroxypinnasterol-3-acetate | (62) | 60 |
| 22-Epi-14α-hydroxypinnasterol-2-acetate | (63) | 61 |
| Podecdysone C | (64) | 62 |
| Polypodine C | (65) | 63 |
| Polypodosaponin A | (66) | 64 |
| Ponasterone C-2-cinnamate | (67) | 65 |
| Ponasteroside A | (68) | 66 |
| Poststerone | (69) | 67 |
| Praemiximisterone | (70) | 68 |
| Pterosterone-24-O-β-D-glucopyranoside | (71) | 69 |
| Rapisterone | (72) | 70 |
| Rubrosterone | (73) | 71 |
| Silenosterone | (74) | 72 |
| Sogdysterone | (75) | 73 |
| Stachysterone A | (76) | 74 |
| Stachysterone B | (77) | 75 |
| Turkesterone | (78) | 76 |
| Viperidone | (79) | 77 |
| Viticosterone E-22-O-benzoate | (80) | 78 |
| Gerardiasterone | (81) | 79 |
| 2-Deoxyecdysone-3-acetate | (82) | 80 |
| 2-Deoxyecdysone-22-benzoate | (83) | 81 |
| Deoxyecdysone-3-β-glucopyranoside | (84) | 82 |
| 2-Deoxyecdysone-25-O-β-glucopyranoside | (85) | 83 |
| 2-Deoxy-20-hydroxyecdysone | (86) | 84 |
| 2-Deoxy-20-hydroxyecdysone-3-acetate | (87) | 85 |
| Sodium ecdysone-22-salfate | (88) | 86 |
| 3-Epi-2-deoxyecdysone | (89) | 87 |
| 14α-hydroxycarpesterol | (90) | 88 |
| 20-Hydroxy-5α-ecdysone | (91) | 89 |
| 20-Hydroxyecdysone-2-acetate | (92) | 90 |
| 20-Hydroxyecdysone-20-O-benzoate | (93) | 91 |
| 20-Hydroxyecdysone-22-O-benzoate | (94) | 92 |
| 20-Hydroxyecdysone-2-cinnamate | (95) | 93 |
| 20-Hydroxyecdysone-3-p-coumarate | (96) | 94 |
| 20-Hydroxyecdysone-3,22-O-α-D-digalactopyranosode | (97) | 95 |
| 20-Hydroxyecdysone-3-O-α-galactopyranoside | (98) | 96 |
| 20-Hydroxyecdysone-25-O-β-glucopyranoside | (99) | 97 |
| 20-Hydroxyecdysone-2,3-acetonide | (100) | 98 |
| 20-Hydroxy-5α-ecdysone-22-O-benzoate | (101) | 99 |
| 20-Hydroxyecdysone-20,22-acetonide | (102) | 100 |
| Integristerone B | (103) | 101 |
| Muristerone A | (104) | 102 |
| Podecdysone B-25-O-β-glucopyranoside | (105) | 103 |
| Polypodine B-2-cinnamate | (106) | 104 |
| Polypodoaurein | (107) | 105 |
| Ecdysone | (108) | 106 |
| 20-Hydroxyecdysone | (109) | 107 |
| 2-Deoxy-20-hydroxyecdysone | (110) | 108 |
| 22-Acetoxy-20-hydroxyecdysone | (111) | 109 |
| Polypodine B | (112) | 110 |
| Polyporusterone A | (113) | 111 |
| Polyporusterone B | (114) | 112 |
| Polyporusterone C | (115) | 113 |
| Polyporusterone D | (116) | 114 |
| Polyporusterone E | (117) | 115 |
| Polyporusterone F | (118) | 116 |
| Polyporusterone G | (119) | 117 |

TABLE 1-continued
List of Steroid Derivatives Used as Blood Flow
Amount-Improving Agent of the Present Invention
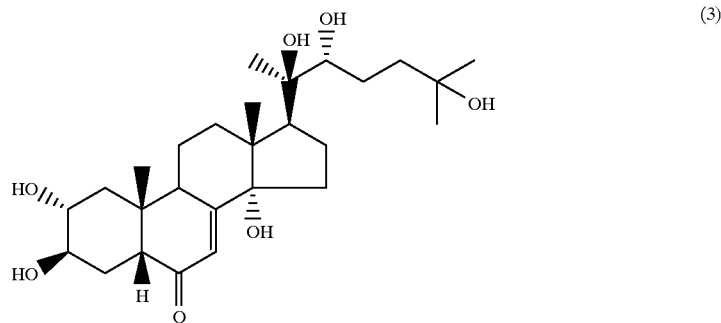
(3)
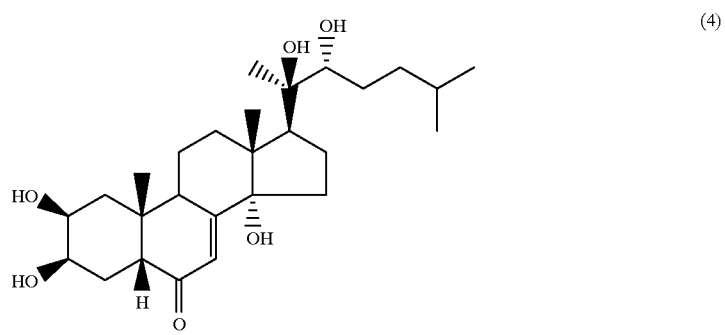
(4)
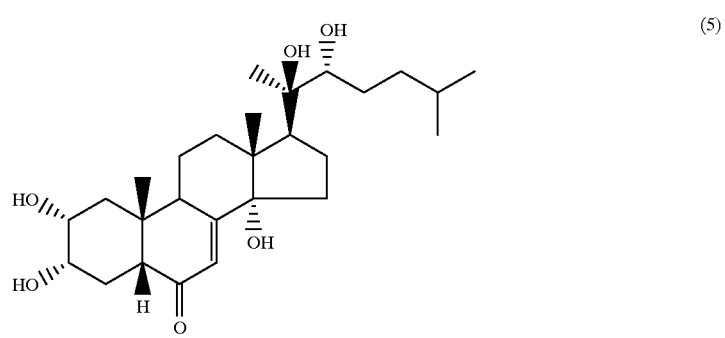
(5)
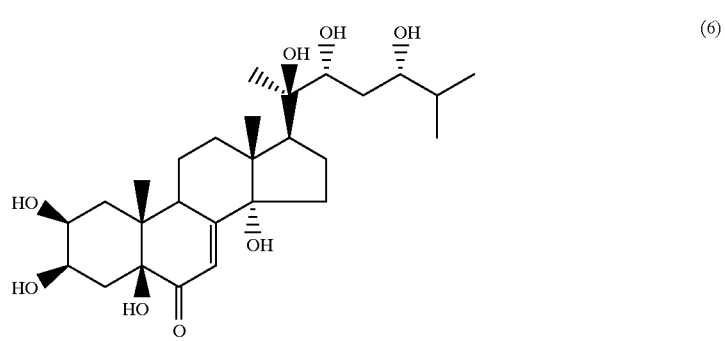
(6)

TABLE 1-continued
List of Steroid Derivatives Used as Blood Flow
Amount-Improving Agent of the Present Invention
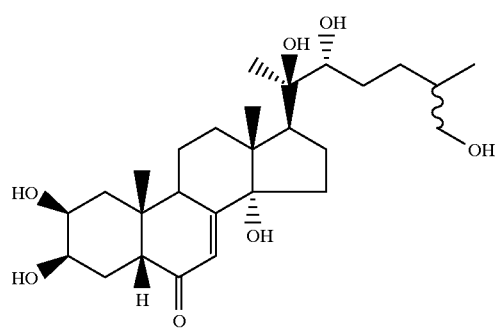
(7)
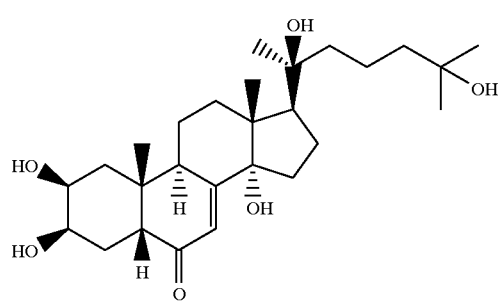
(8)
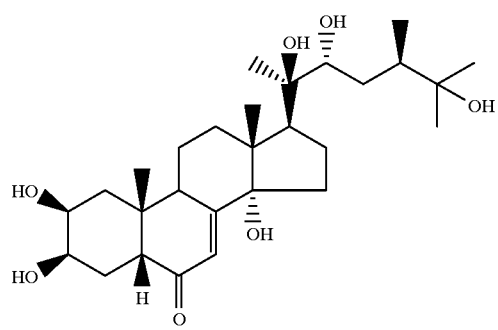
(9)
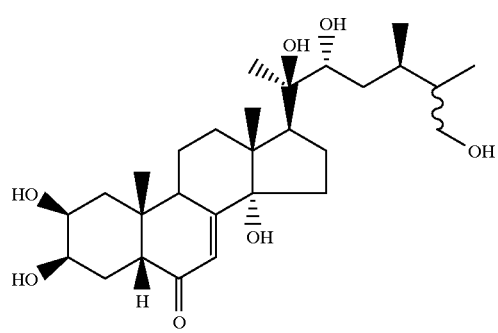
(10)

TABLE 1-continued
List of Steroid Derivatives Used as Blood Flow
Amount-Improving Agent of the Present Invention
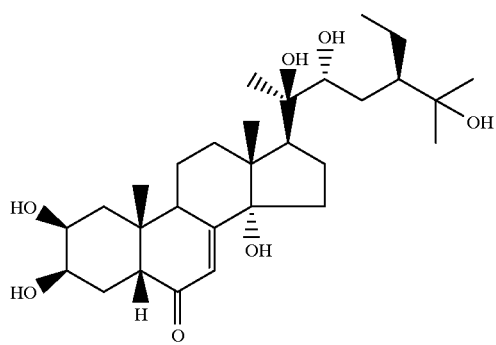
(11)
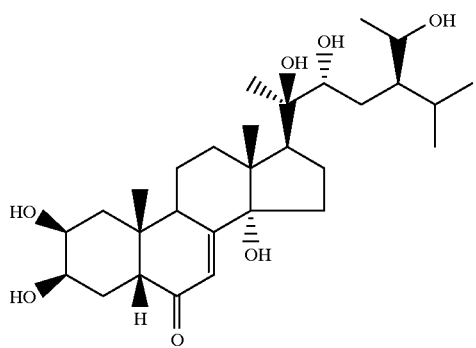
(12)
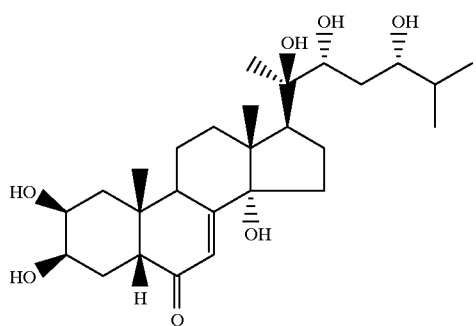
(13)
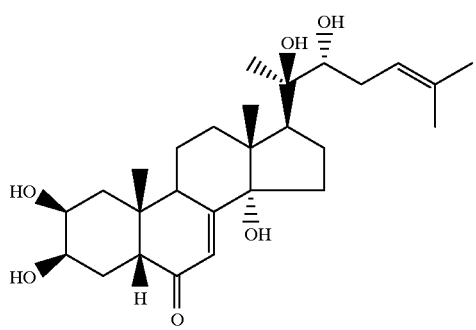
(14)

TABLE 1-continued
List of Steroid Derivatives Used as Blood Flow
Amount-Improving Agent of the Present Invention
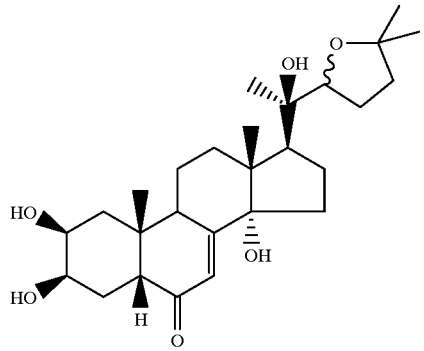
(15)
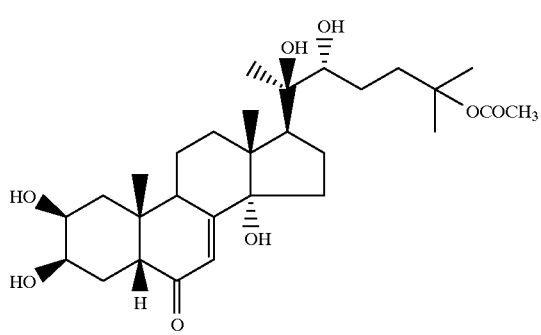
(16)
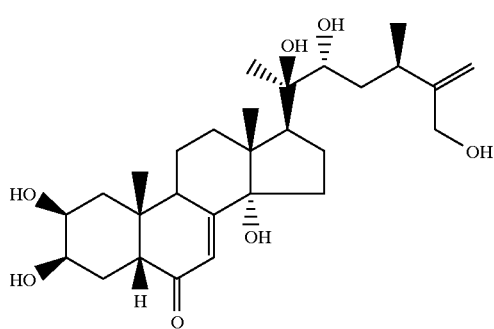
(17)
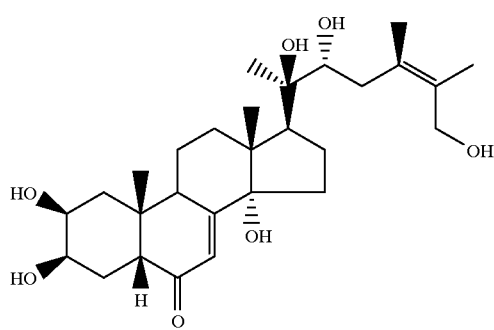
(18)

TABLE 1-continued
List of Steroid Derivatives Used as Blood Flow
Amount-Improving Agent of the Present Invention
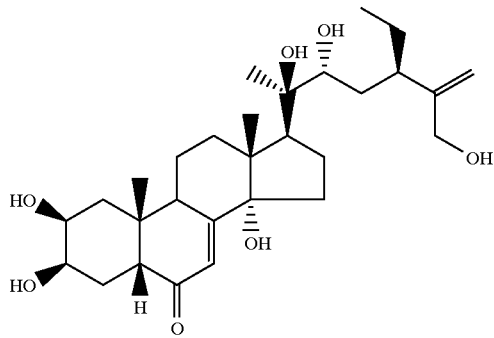
(19)
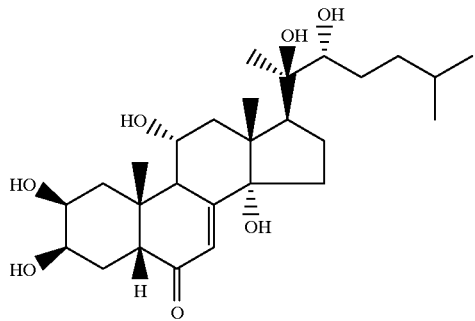
(20)
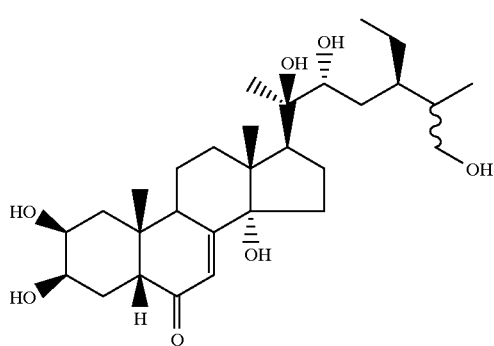
(21)
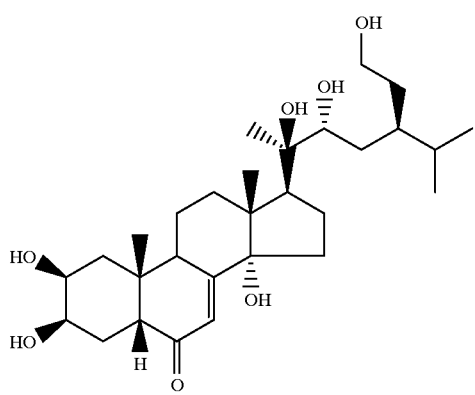
(22)

TABLE 1-continued
List of Steroid Derivatives Used as Blood Flow
Amount-Improving Agent of the Present Invention
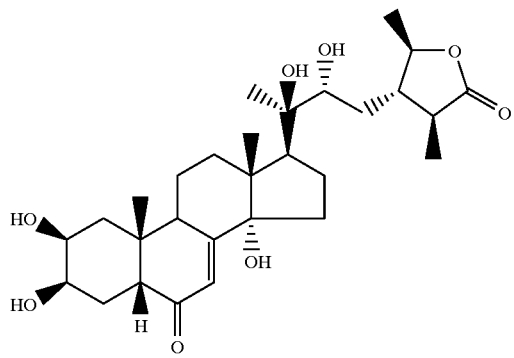
(23)
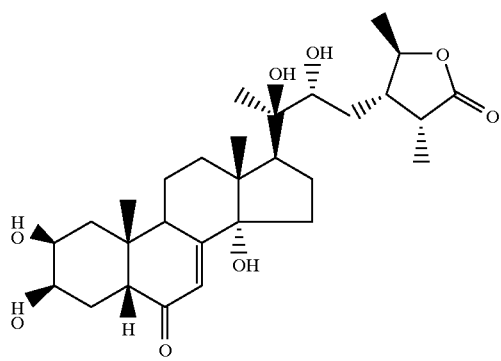
(24)
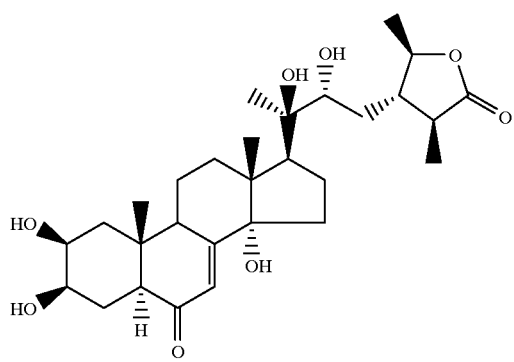
(25)
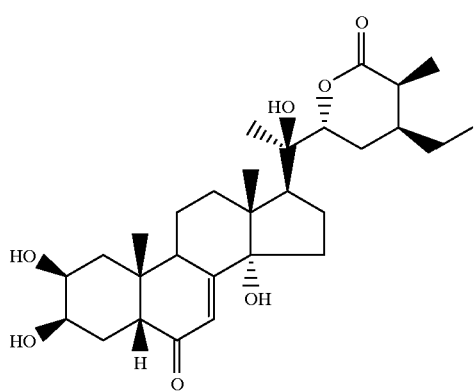
(26)

TABLE 1-continued
List of Steroid Derivatives Used as Blood Flow
Amount-Improving Agent of the Present Invention
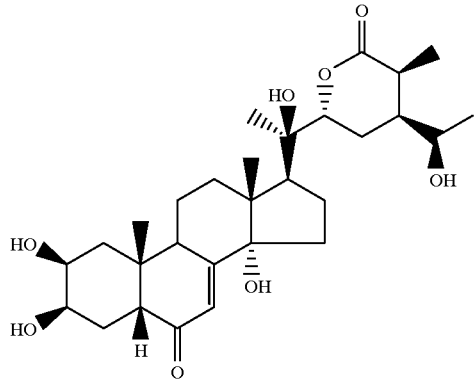
(27)
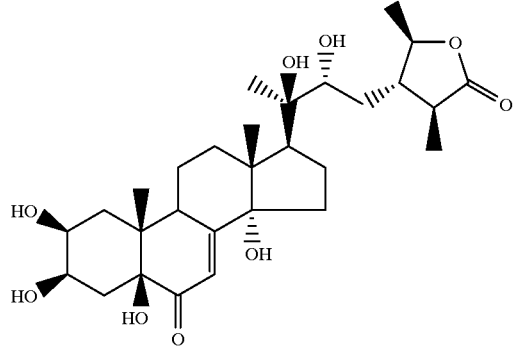
(28)
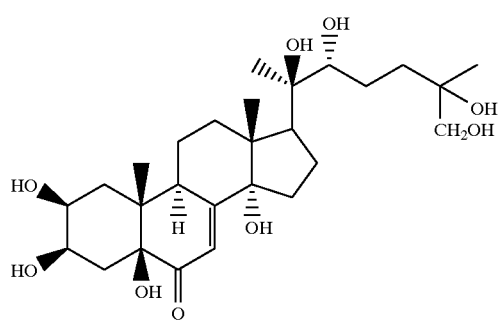
(29)
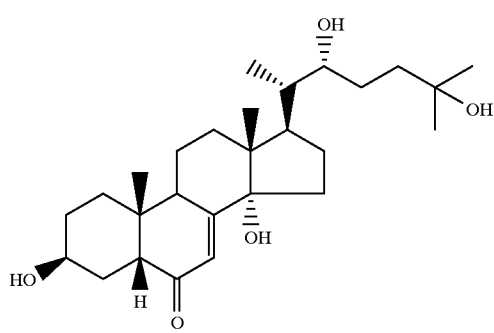
(30)

TABLE 1-continued
List of Steroid Derivatives Used as Blood Flow
Amount-Improving Agent of the Present Invention
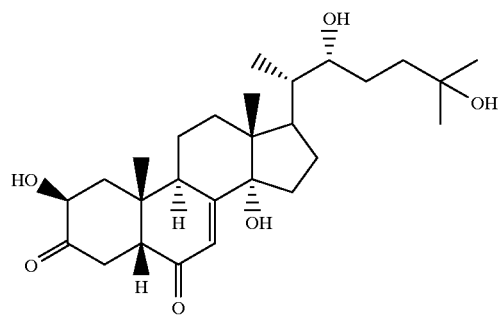
(31)
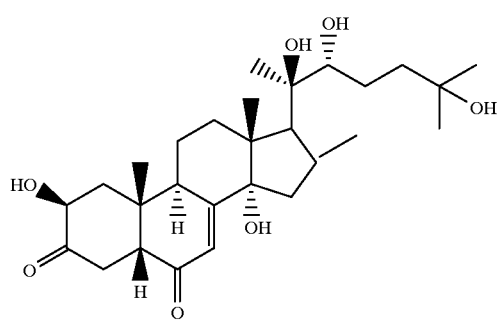
(32)
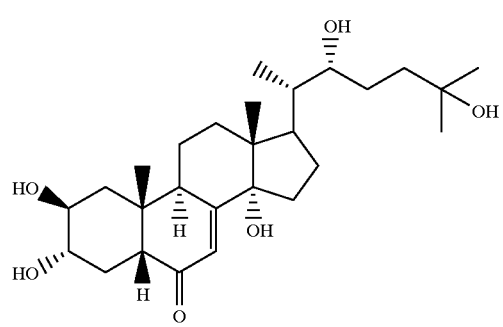
(33)
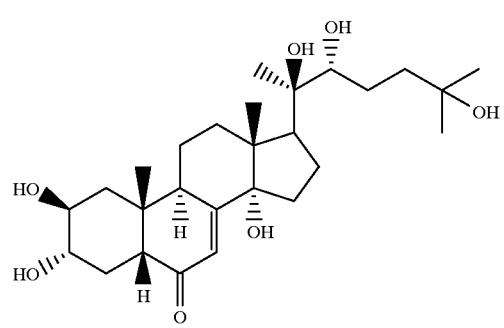
(34)

TABLE 1-continued
List of Steroid Derivatives Used as Blood Flow
Amount-Improving Agent of the Present Invention
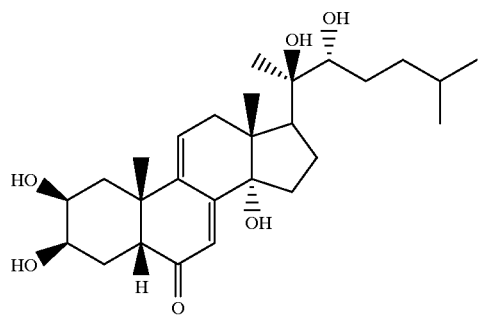
(35)
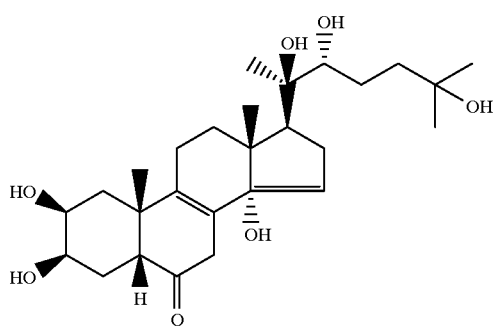
(36)
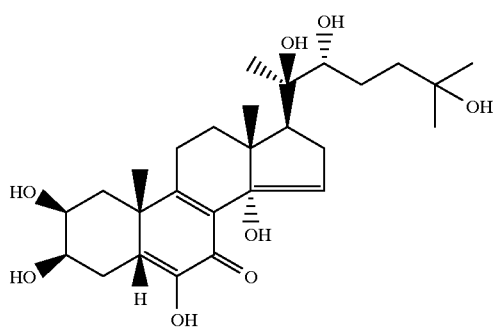
(37)
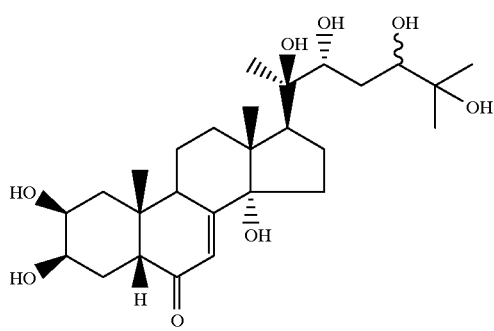
(38)

TABLE 1-continued
List of Steroid Derivatives Used as Blood Flow
Amount-Improving Agent of the Present Invention
(39)
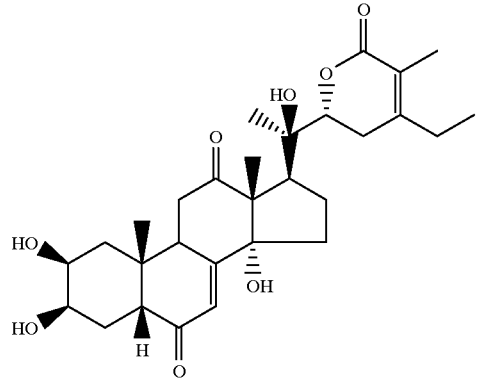
(40)
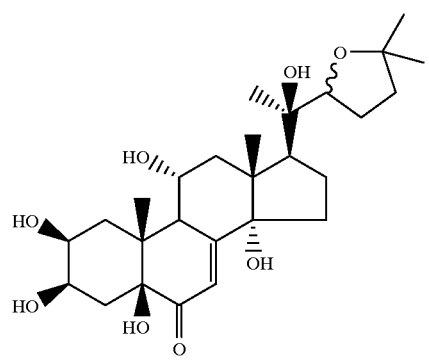
(41)
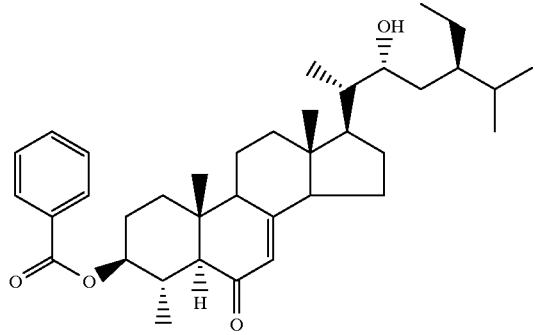
(42)
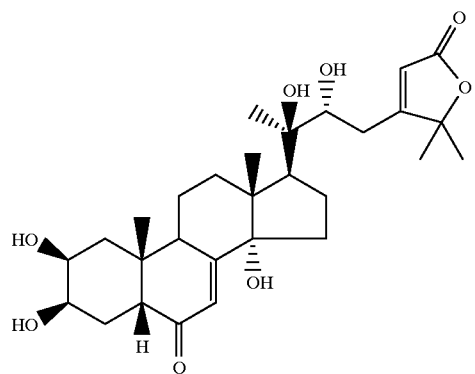

TABLE 1-continued
List of Steroid Derivatives Used as Blood Flow
Amount-Improving Agent of the Present Invention
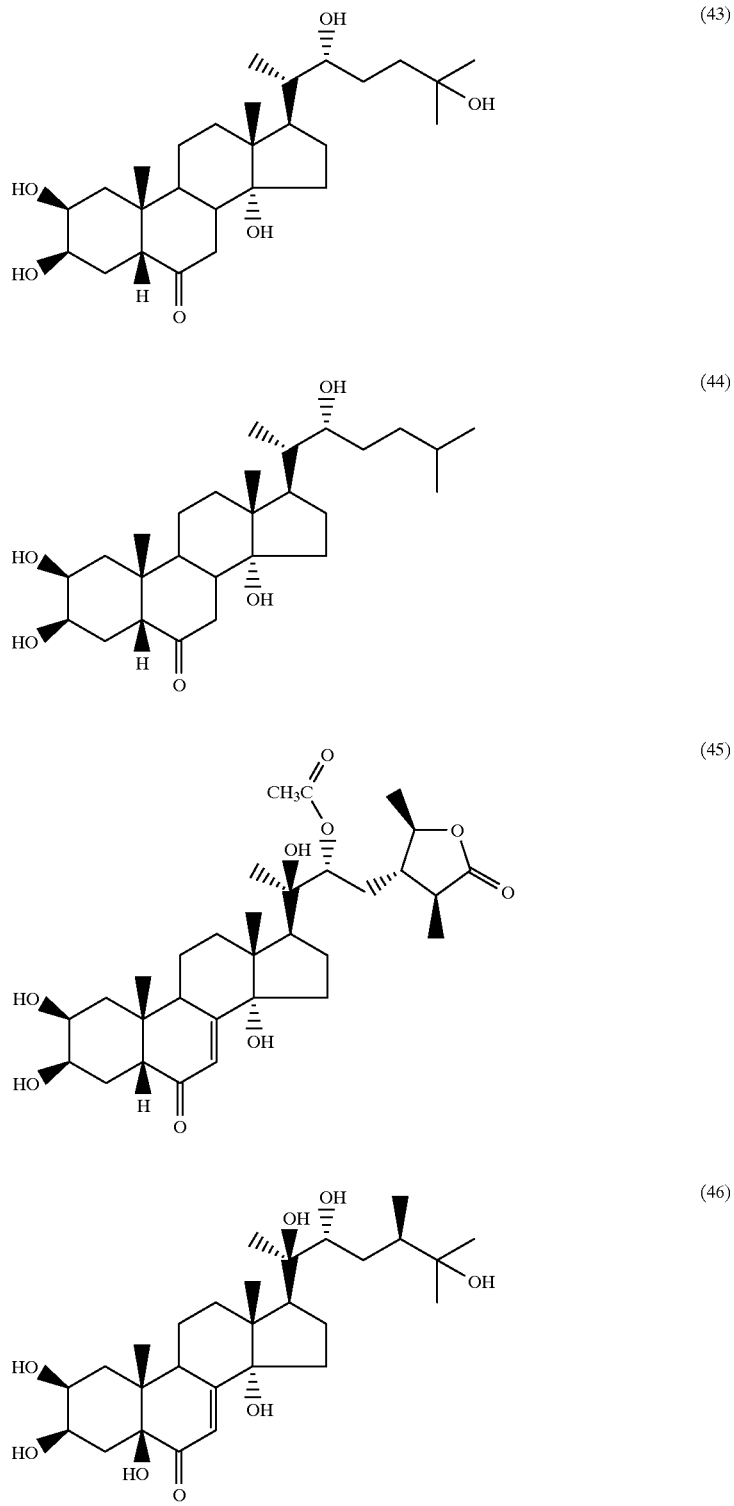

TABLE 1-continued
List of Steroid Derivatives Used as Blood Flow
Amount-Improving Agent of the Present Invention
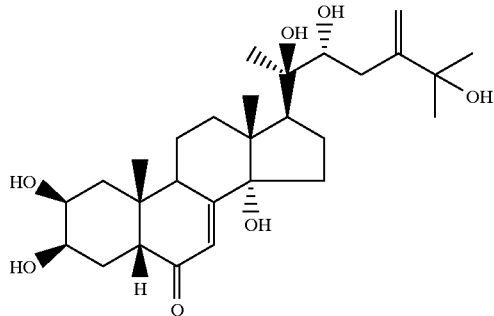
(47)
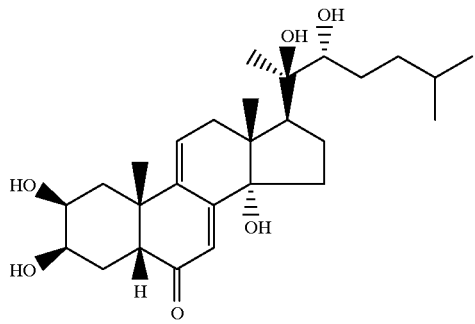
(48)
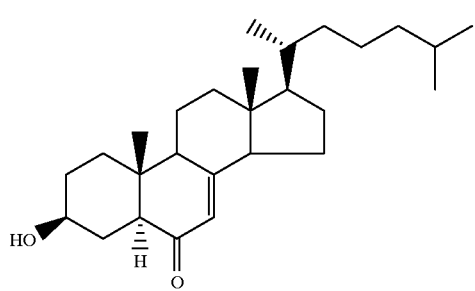
(49)
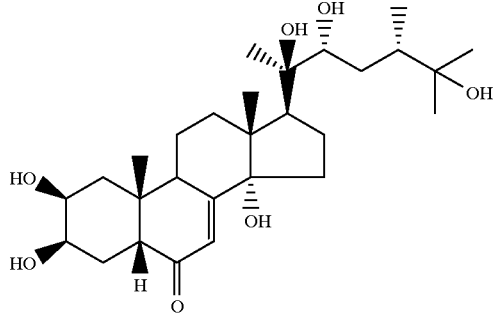
(50)

TABLE 1-continued
List of Steroid Derivatives Used as Blood Flow
Amount-Improving Agent of the Present Invention
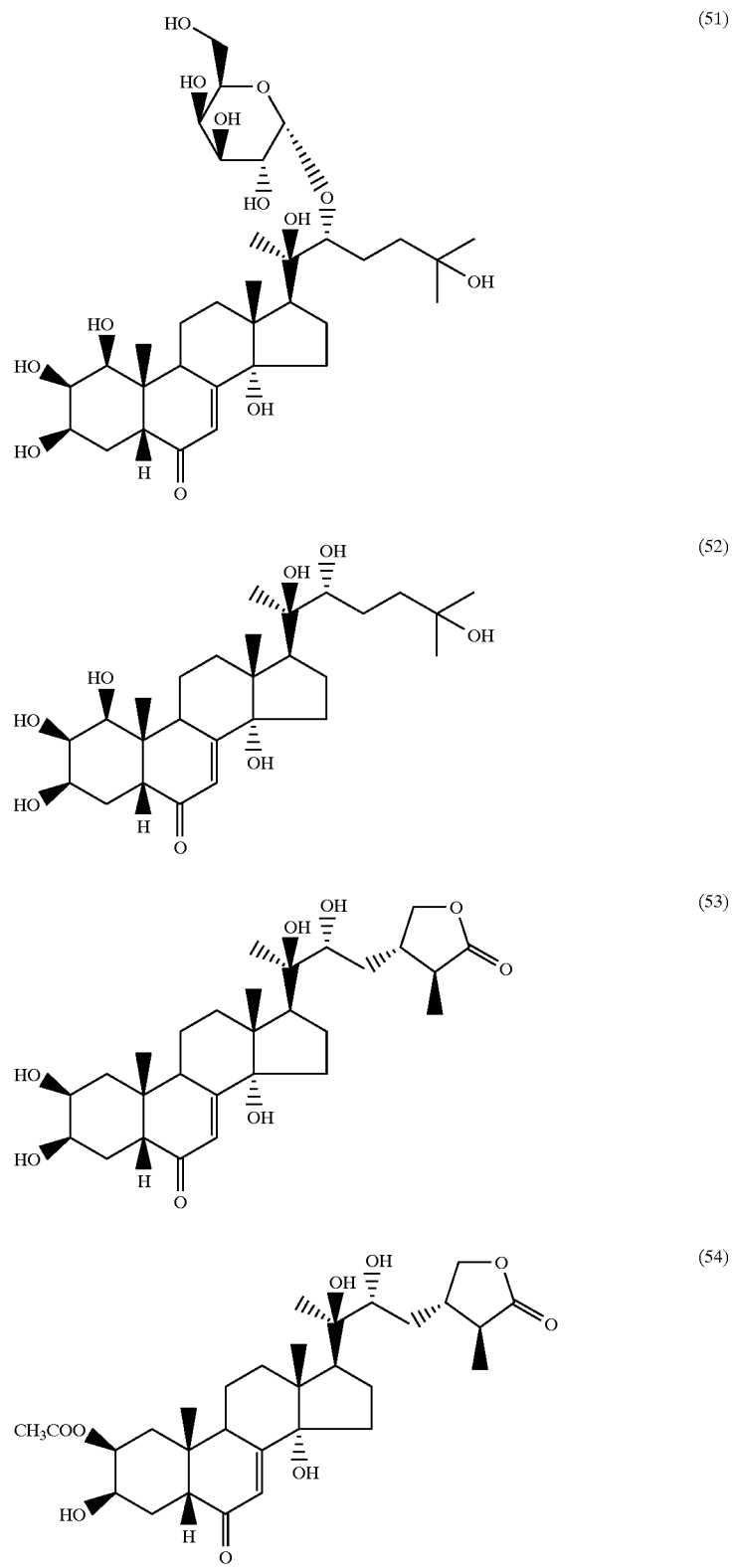

TABLE 1-continued
List of Steroid Derivatives Used as Blood Flow
Amount-Improving Agent of the Present Invention
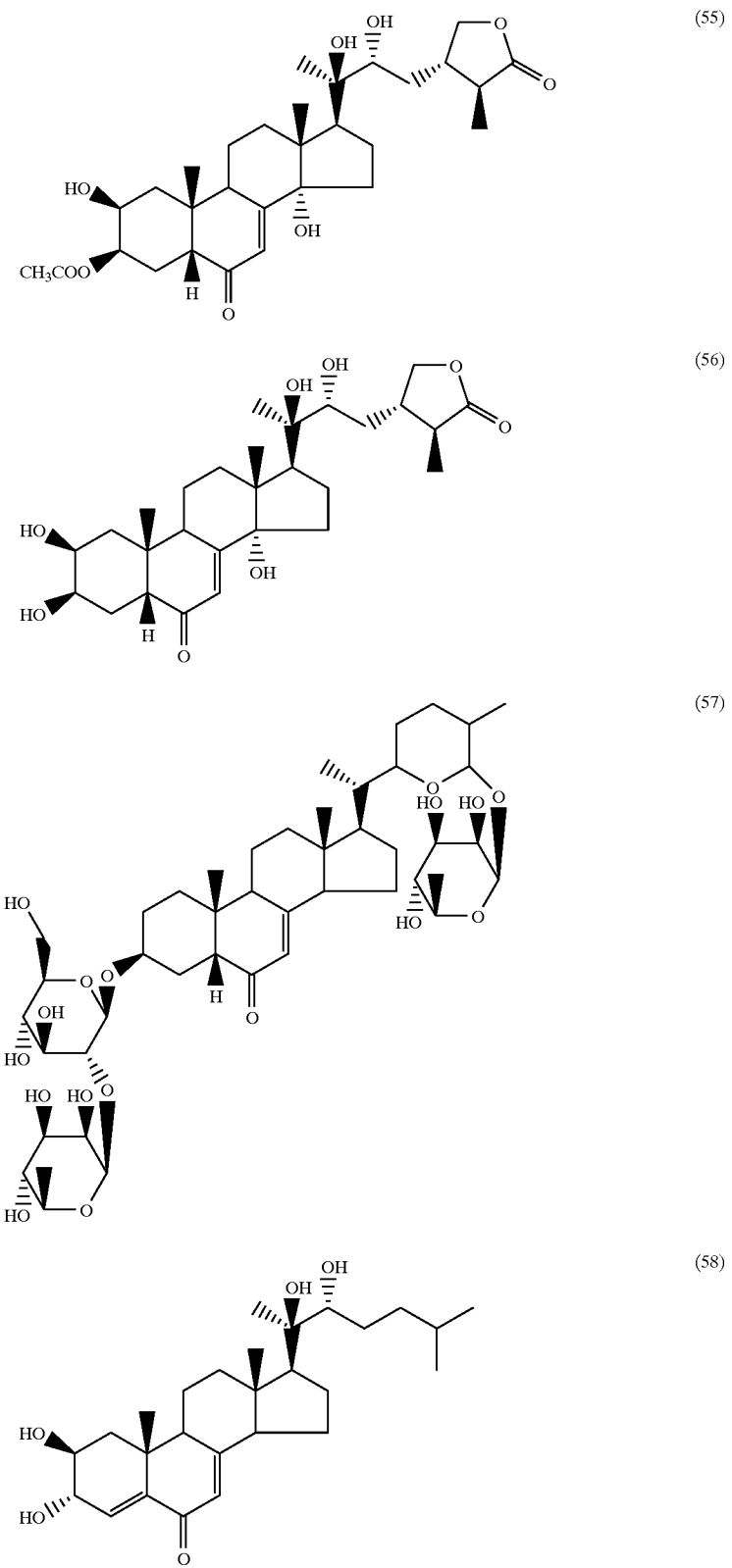
(55)
(56)
(57)
(58)

TABLE 1-continued
List of Steroid Derivatives Used as Blood Flow
Amount-Improving Agent of the Present Invention
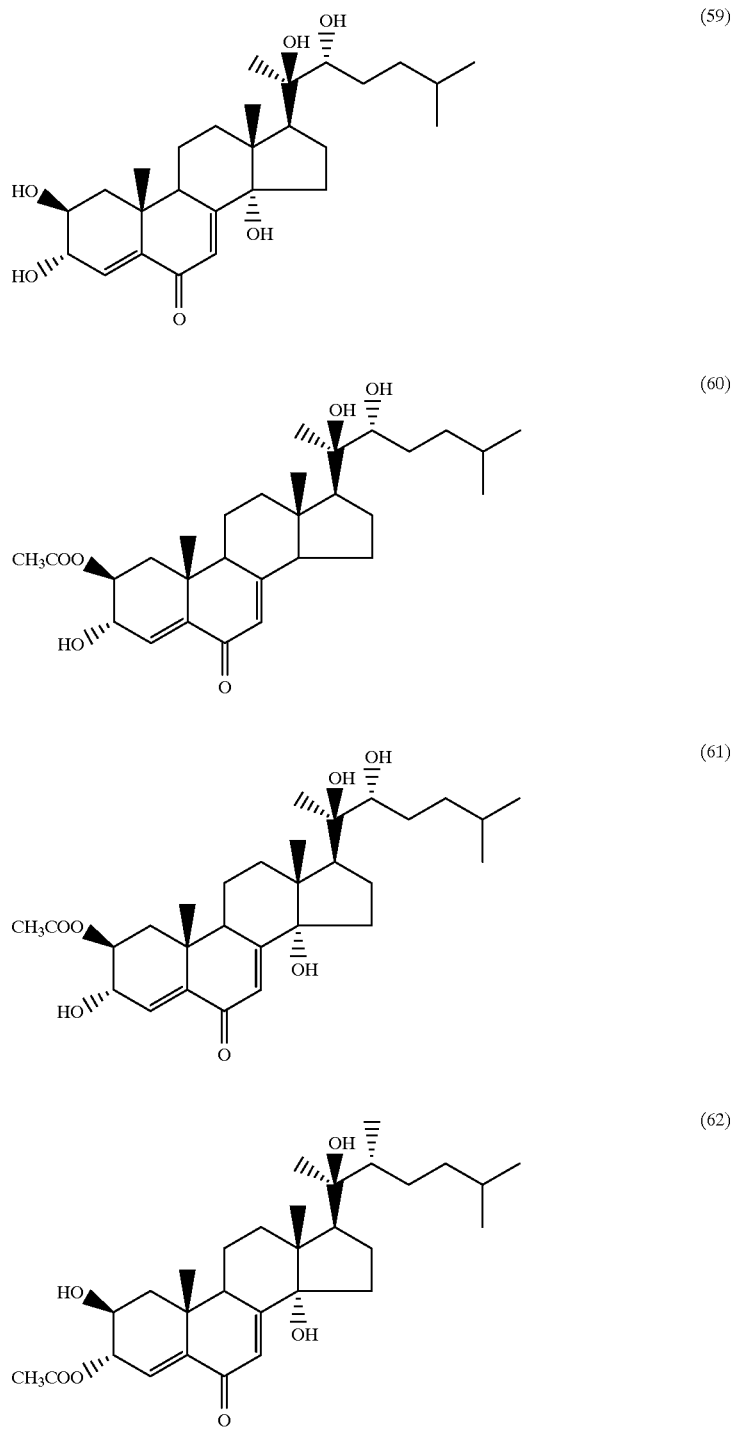
(59)
(60)
(61)
(62)

TABLE 1-continued
List of Steroid Derivatives Used as Blood Flow
Amount-Improving Agent of the Present Invention
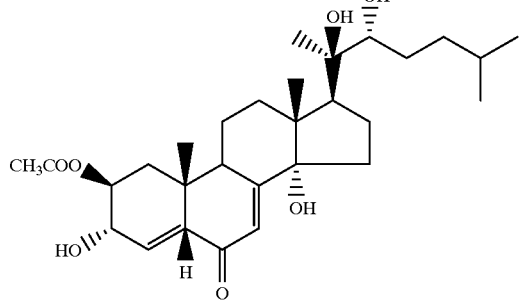
(63)
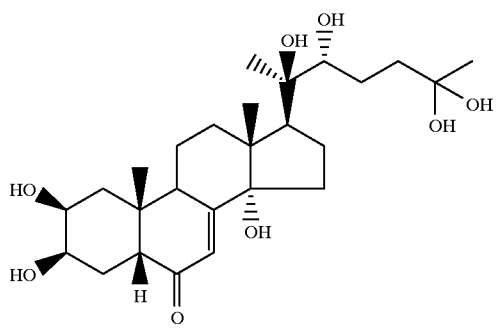
(64)
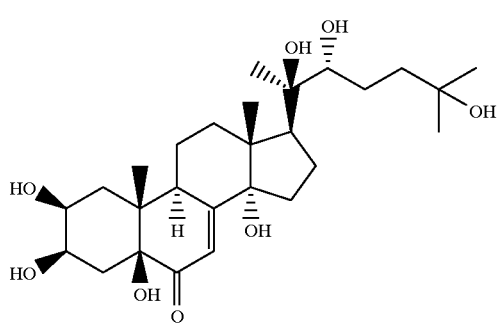
(65)
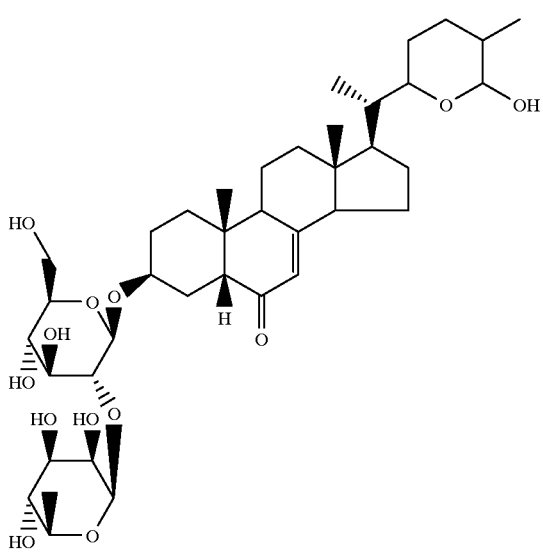
(66)

TABLE 1-continued
List of Steroid Derivatives Used as Blood Flow
Amount-Improving Agent of the Present Invention
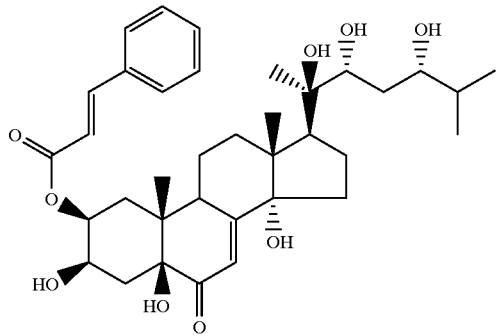
(67)
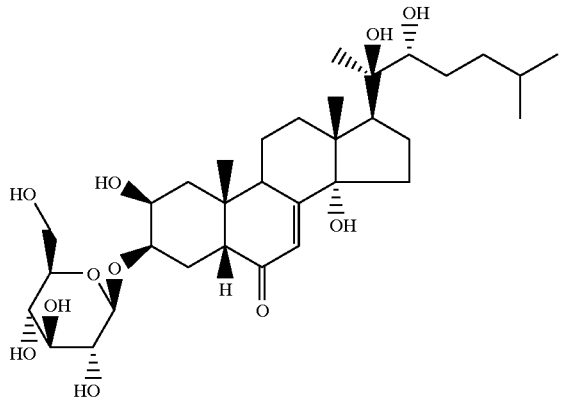
(68)
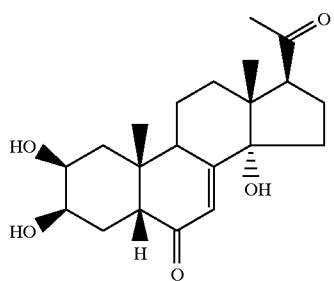
(69)
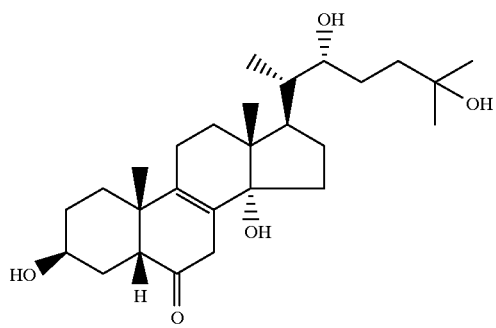
(70)

TABLE 1-continued
List of Steroid Derivatives Used as Blood Flow
Amount-Improving Agent of the Present Invention
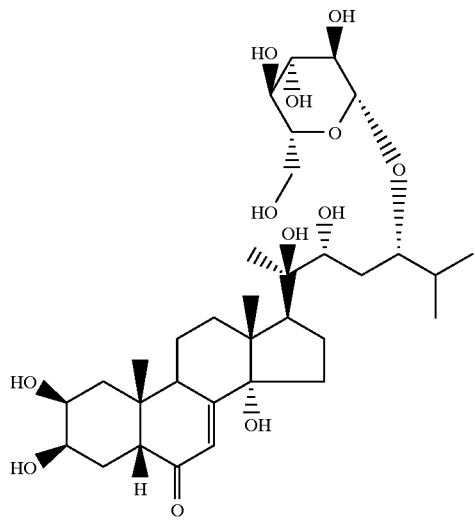
(71)
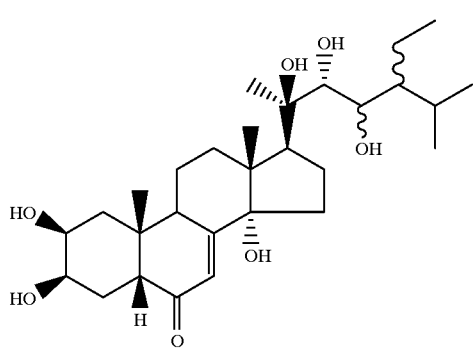
(72)
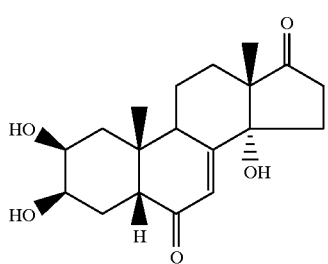
(73)
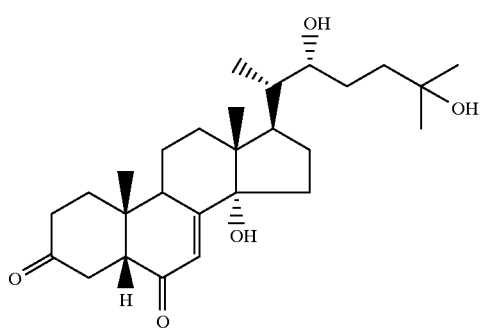
(74)

TABLE 1-continued
List of Steroid Derivatives Used as Blood Flow Amount-Improving Agent of the Present Invention
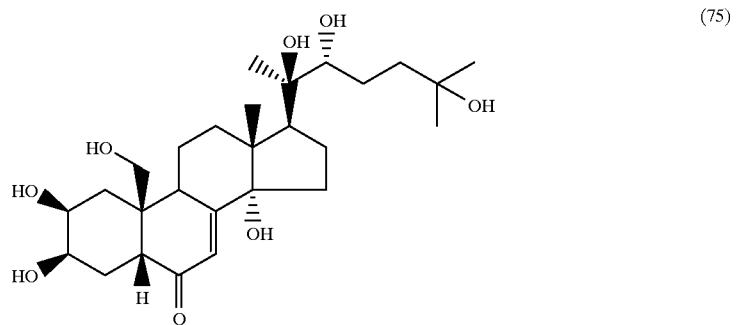
(75)
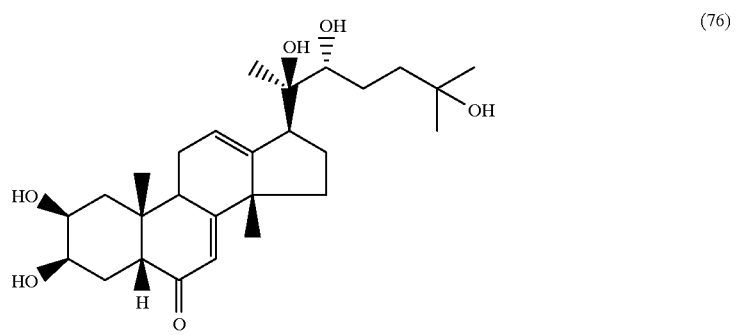
(76)
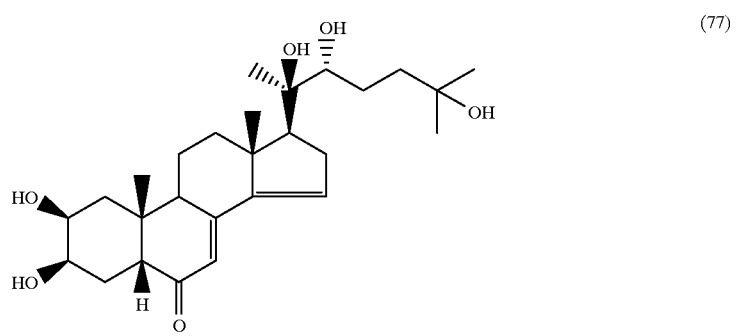
(77)
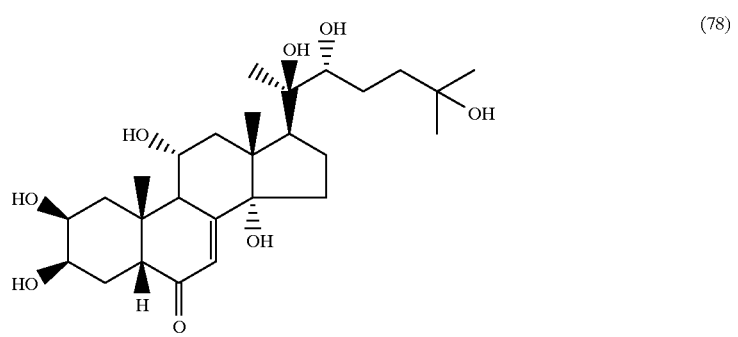
(78)

TABLE 1-continued
List of Steroid Derivatives Used as Blood Flow
Amount-Improving Agent of the Present Invention
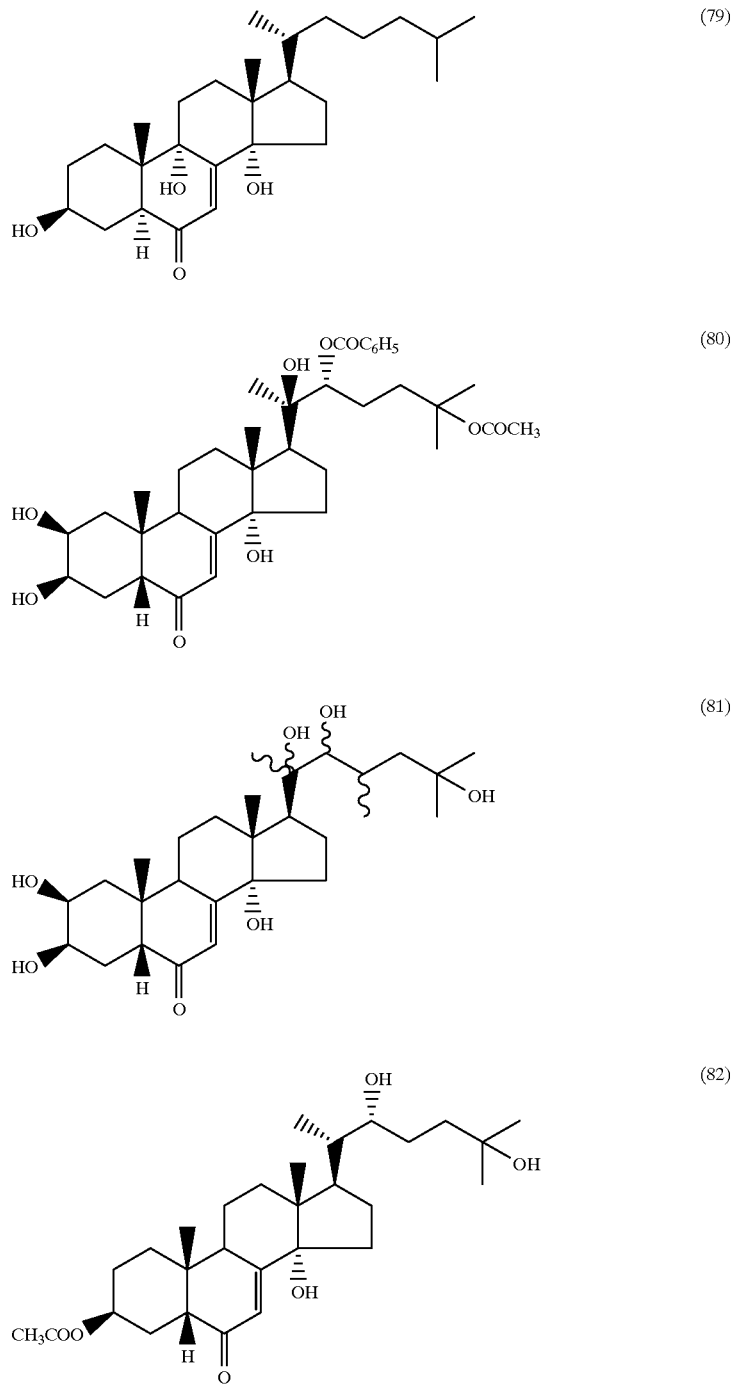

TABLE 1-continued
List of Steroid Derivatives Used as Blood Flow
Amount-Improving Agent of the Present Invention
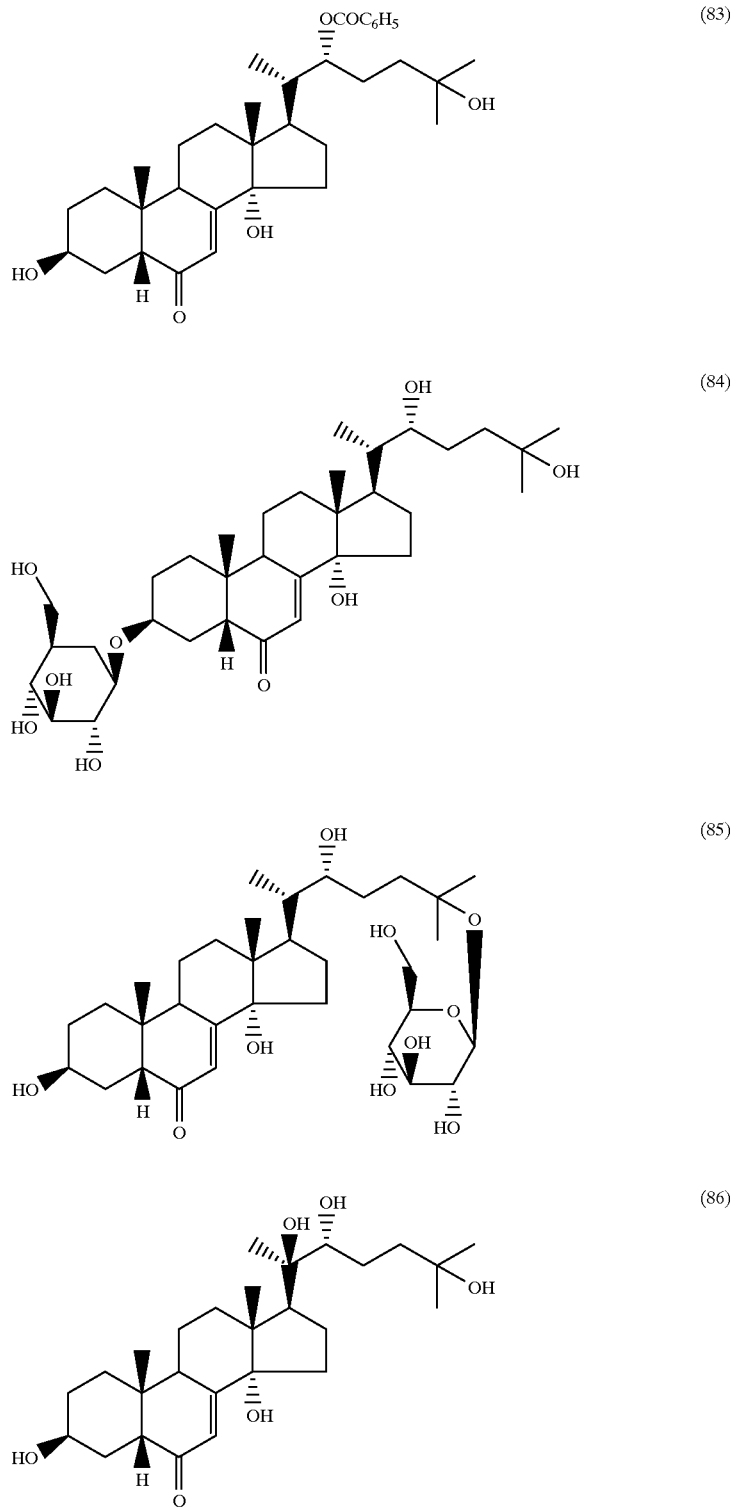

TABLE 1-continued
List of Steroid Derivatives Used as Blood Flow
Amount-Improving Agent of the Present Invention
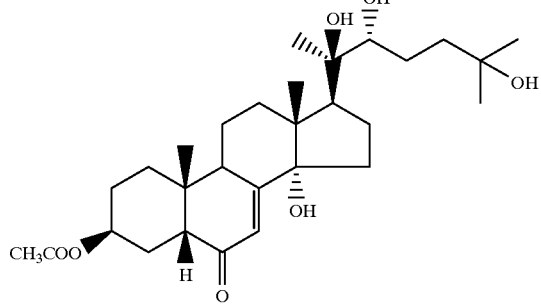
(87)
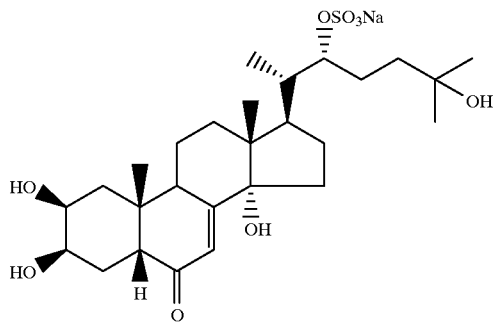
(88)
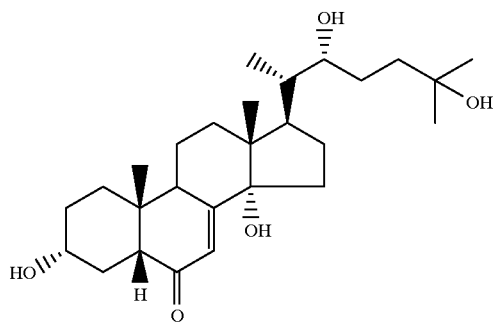
(89)
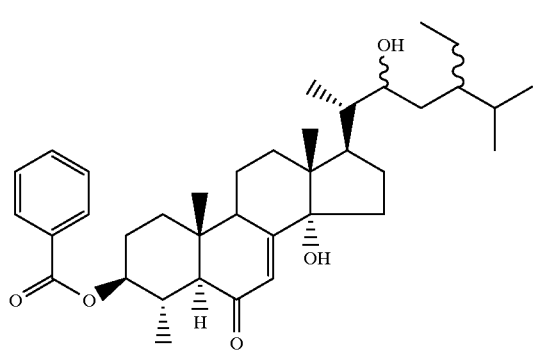
(90)

TABLE 1-continued
List of Steroid Derivatives Used as Blood Flow
Amount-Improving Agent of the Present Invention
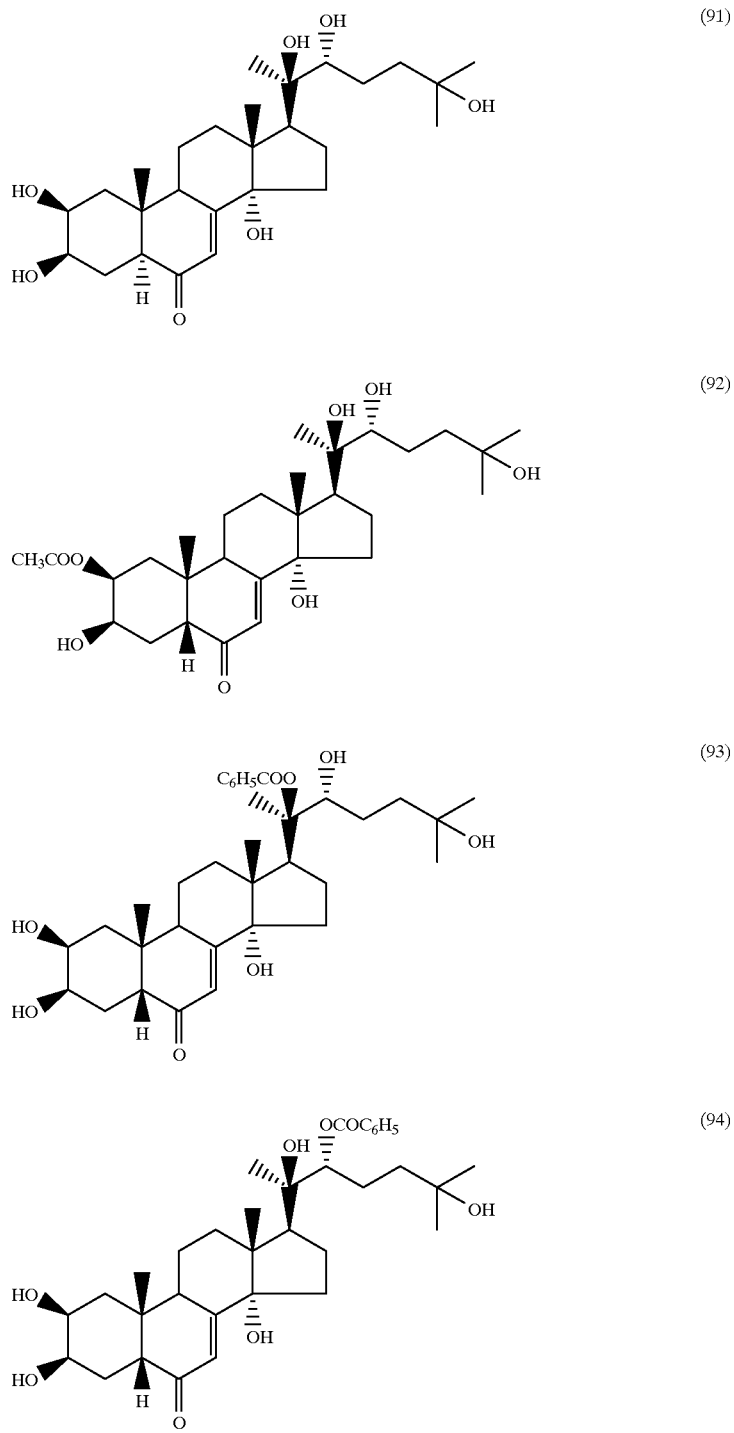

TABLE 1-continued
List of Steroid Derivatives Used as Blood Flow
Amount-Improving Agent of the Present Invention
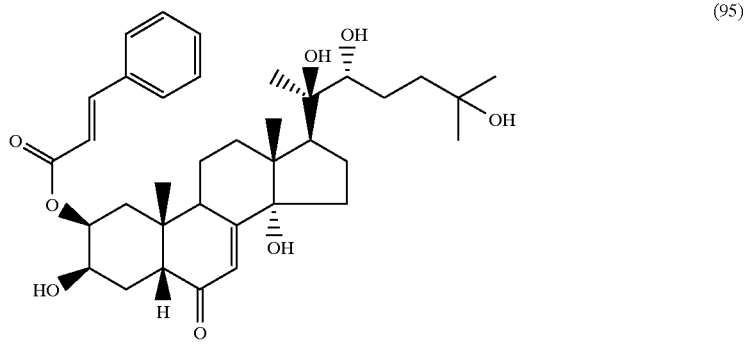
(95)
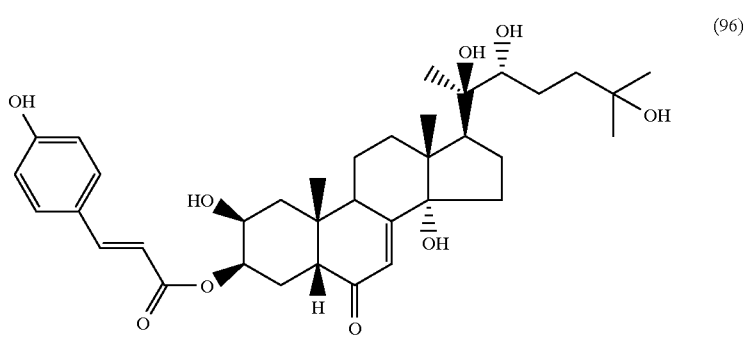
(96)
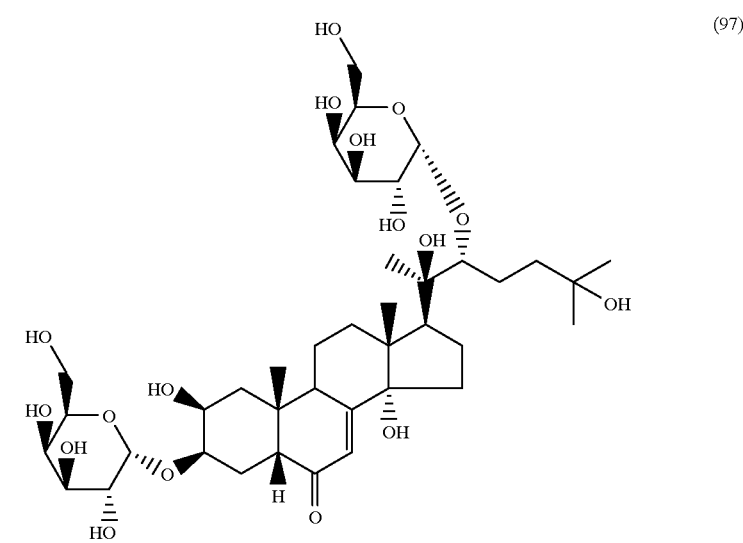
(97)
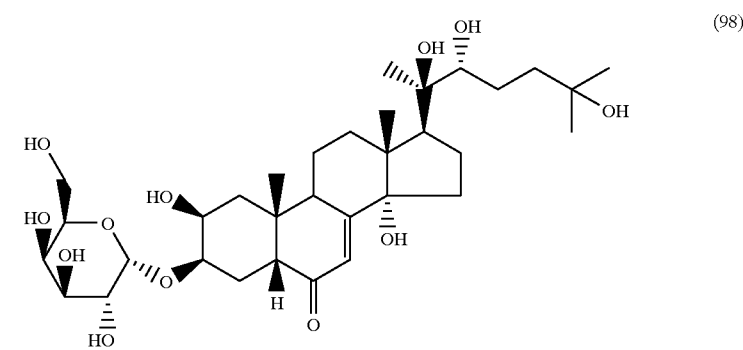
(98)

TABLE 1-continued
List of Steroid Derivatives Used as Blood Flow
Amount-Improving Agent of the Present Invention
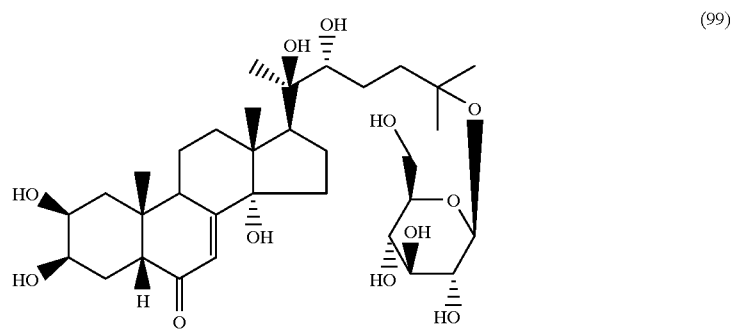
(99)
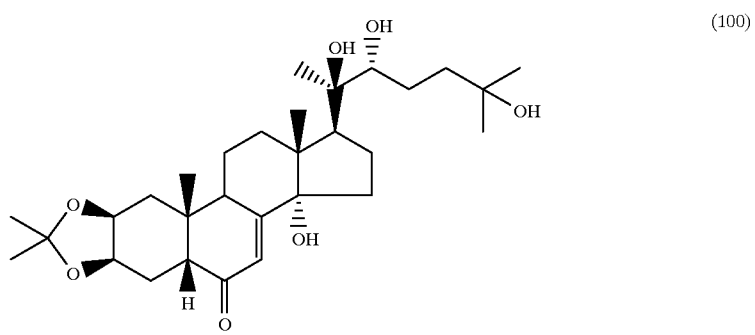
(100)
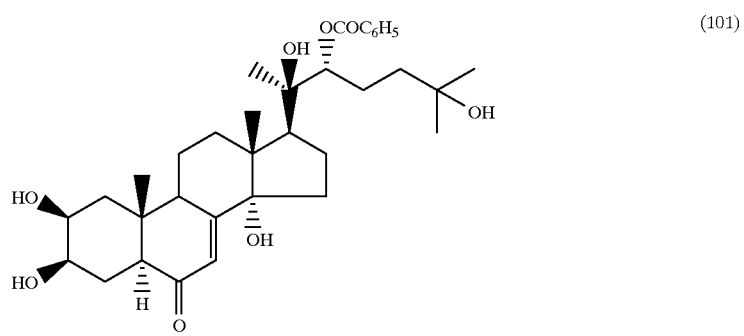
(101)
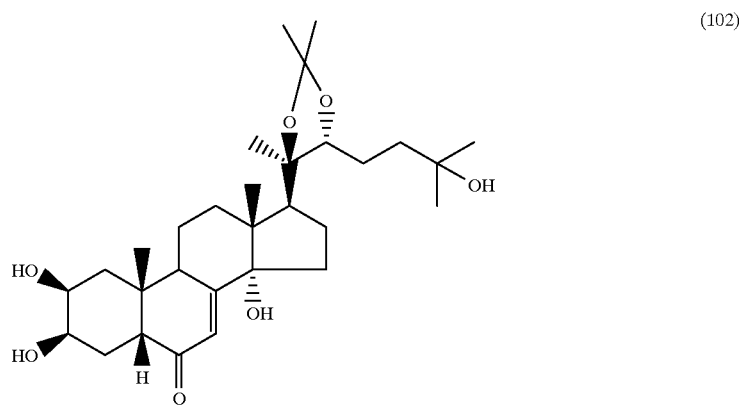
(102)

TABLE 1-continued
List of Steroid Derivatives Used as Blood Flow
Amount-Improving Agent of the Present Invention
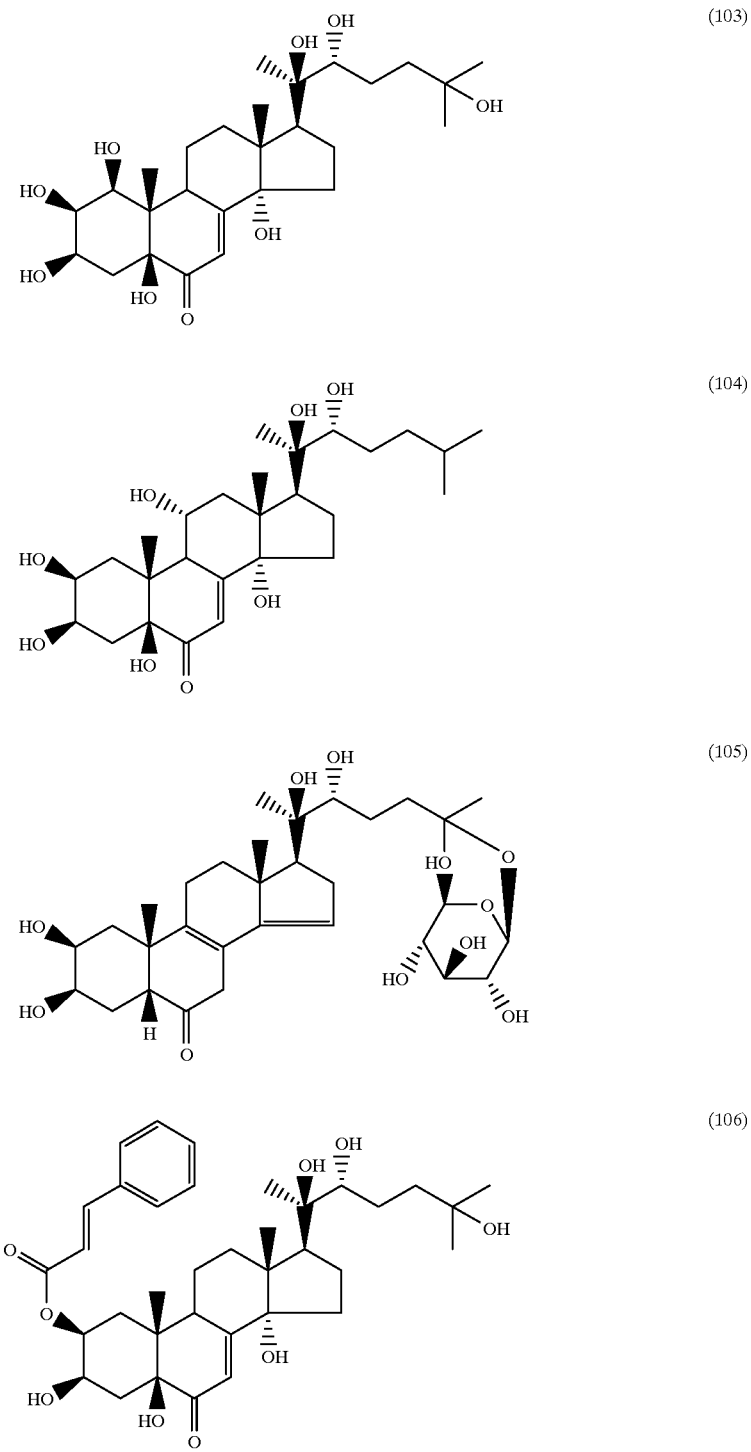

TABLE 1-continued
List of Steroid Derivatives Used as Blood Flow
Amount-Improving Agent of the Present Invention
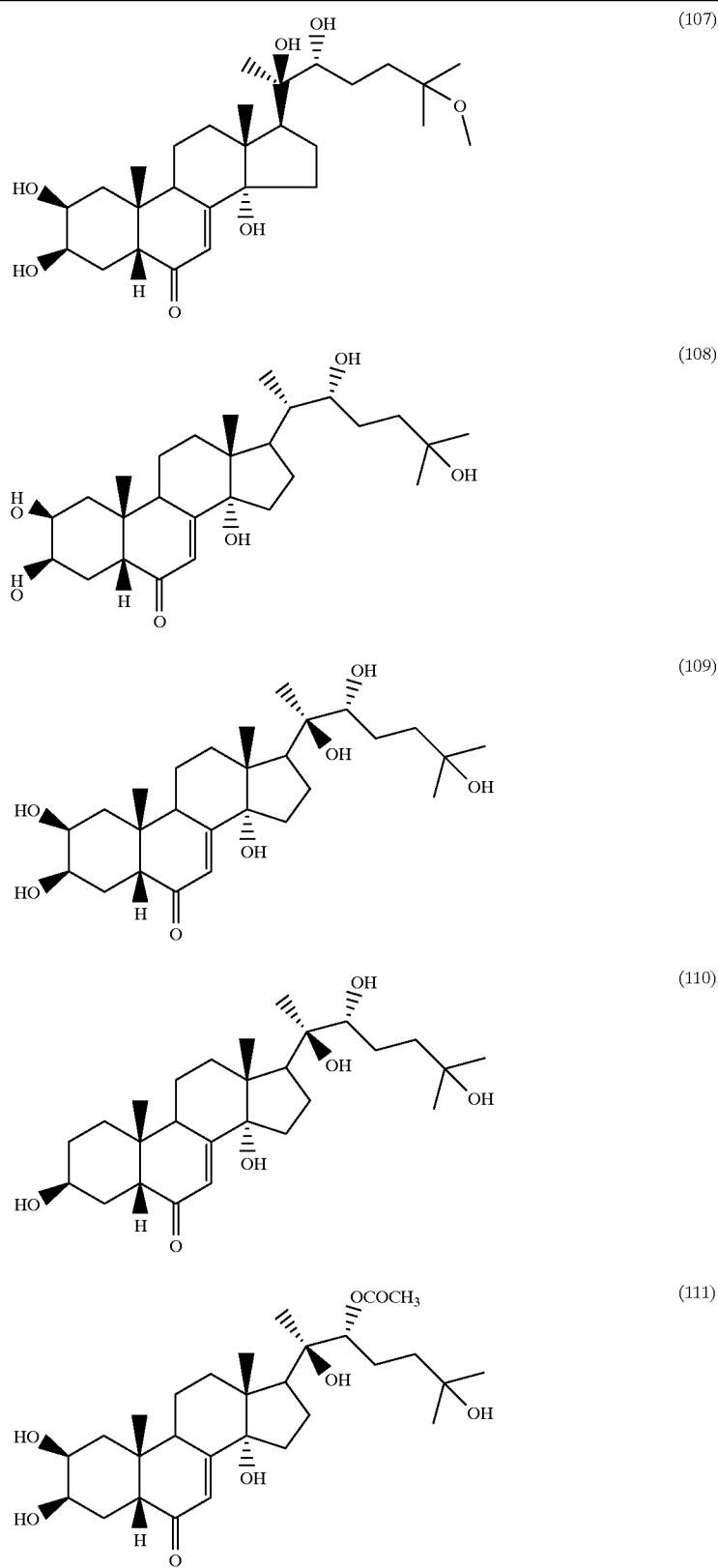

TABLE 1-continued
List of Steroid Derivatives Used as Blood Flow
Amount-Improving Agent of the Present Invention
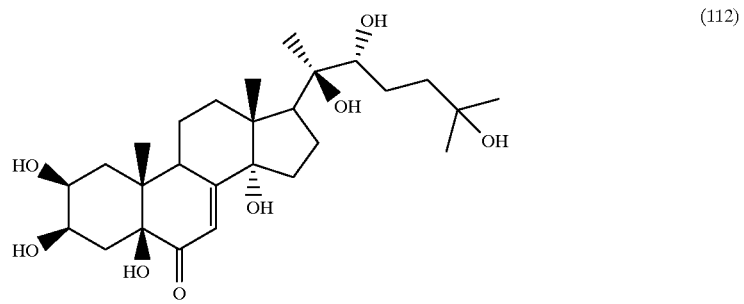
(112)
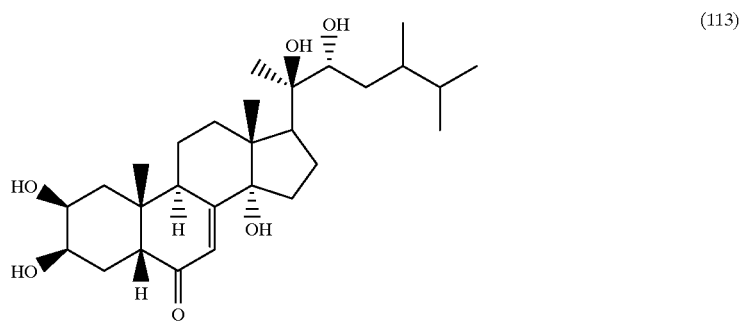
(113)
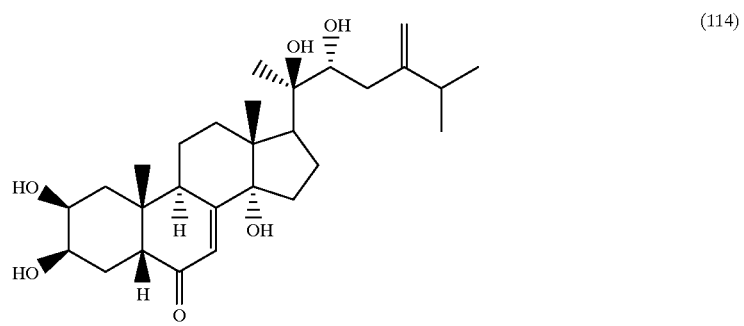
(114)
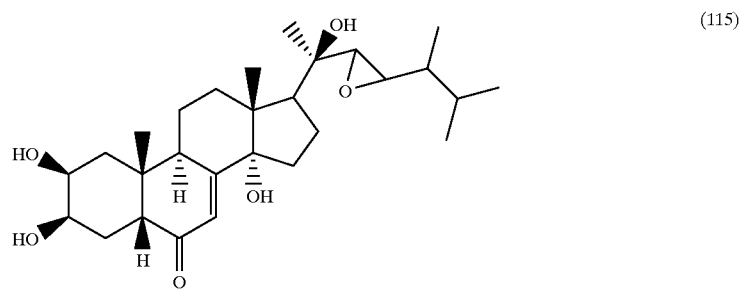
(115)

TABLE 1-continued

List of Steroid Derivatives Used as Blood Flow
Amount-Improving Agent of the Present Invention

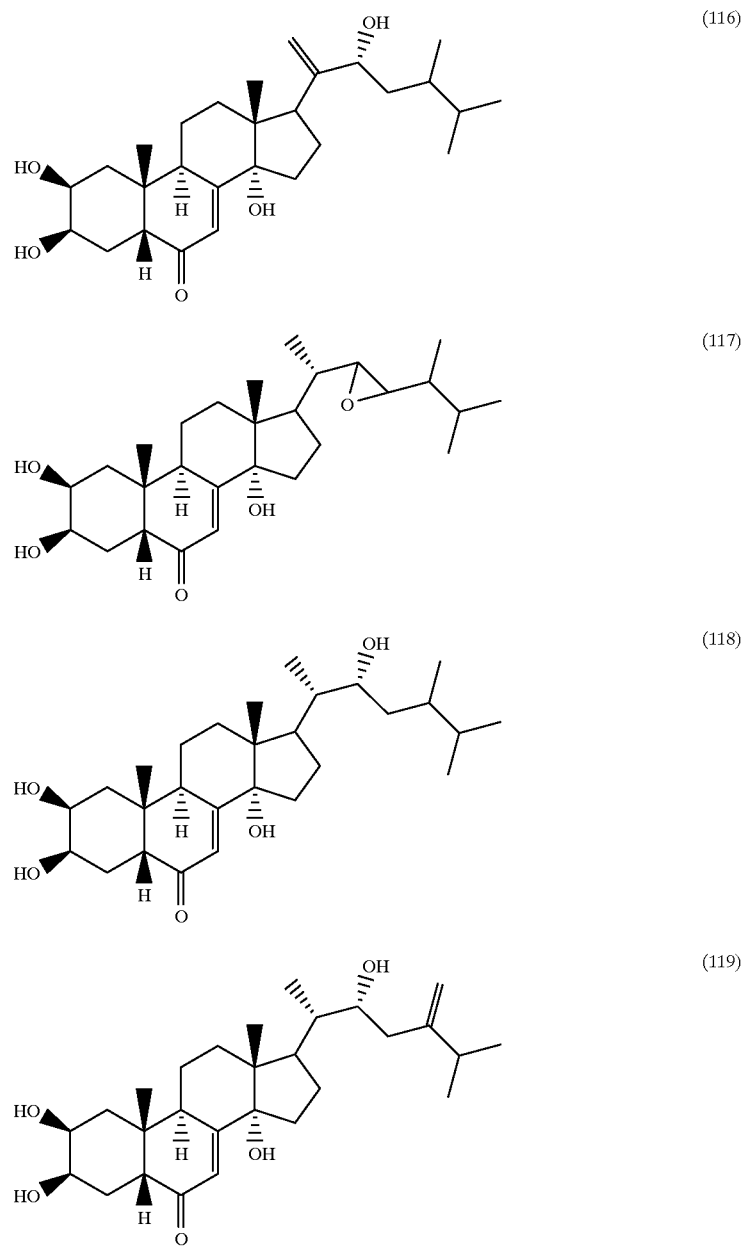

(116)

(117)

(118)

(119)

Those which are more preferable to be practically used as the blood flow amount-improving agent of the present invention among the steroid derivatives described above are, for example, Paristerone (Steroid 1), Ponasterone A (Steroid 2), Inokosterone (Steroid 5), Makisterone A (Steroid 7), Makisterone C (Steroid 9), 3-Epiecdysone (Steroid 31), Cheilanthone B (Steroid 42), 24(28)-Dehydromakisterone A (Steroid 45), Integristerone A-22-O-α-D-galactopyranoside (Steroid 49), 14α-Hydroxypinnasterol-2-acetate (Steroid 59), Polypodosaponin A (Steroid 64), Ponasteroside A (Steroid 66), Pterosterone-24-O-β-D-glucopyranoside (Steroid 69), Viticosterone E-22-O-benzoate (Steroid 78), Deoxyecdysone-3-β-glucopyranoside (Steroid 82), 2-Deoxyecdysone-25-O-β-glucopyranoside (Steroid 83), 20-Hydroxyecdysone-3-O-α-galactopyranoside (Steroid 96), and Polyporusterone A (Steroid 111) because they exhibit an excellent blood flow amount-improving function and an excellent hair growth-facilitating function even at an extremely low concentration, as well as Abutasterone (Steroid 36), Ecdysone (Steroid 106), 20-Hydroxyecdysone (Steroid 107), and Polypodine B (Steroid 110) because they exist in large amounts in natural products, or they are commercially available everywhere, and hence they are easily obtainable.

Any of the steroid derivatives described above used in the present invention is a known substance. They are known to exist in various animals and plants. The animals and plants which contain various species of the steroid derivatives include, for example, plants such as those belonging to Caryophyllaceae, Filicales, Labiatae (Lamiaceae), and Verbenaceae; and animals such as those belonging to Cyathula. Table 2 shows animals and plants which serve as origins of the various steroid derivatives shown in Table 1 described above preferably used as the blood flow amount-improving agent of the present invention.

Among the steroid derivatives shown in Table 1 described above, Ecdysone (Steroid 106), 20-Hydroxyecdysone (Steroid 107), 2-Deoxy-20-hydroxyecdysone (Steroid 108), 22-Acetoxy-20-hydroxyecdysone (Steroid 109), and Polypodine B (Steroid 110) are commercially available, for example, from Aldrich. They can be used as the blood flow amount-improving agent of the present invention. Accordingly, they are not shown in Table 2.

TABLE 2

Animal and Plant Origins of Various Steroid Derivatives

| Animal and Plant Origins | Steroid No. |
|---|---|
| Paris polyphylla | 1 |
| Podocarpus nakaii | 2, 3, 4 |
| Achyranthes fauriei | 5, 29, 30, 31, 32, 89 |
| Taxus cuspidata | 6 |
| Podocarpus macrophyllus | 7, 8, 9, 10, 34, 39, 62 |
| Onoclea sensibilis | 11 |
| Stachyrus praecox | 12, 13, 74, 75 |
| Vitex megapotamica | 14 |
| Blechnum niponicum | 15, 16, 82, 83, 87 |
| Ajuga decumbens | 17, 18, 37, 38 |
| Cyathula officinalis | 19, 20, 21, 22, 23, 24 25, 26, 67 |
| Polypodium vulgare | 27, 64 |
| Silene otites | 28, 84 |
| Ipomoea calonyction | 33, 35, 102 |
| Abuta velutina | 36 |
| Rhaponticum carthamoides | 40, 45 |
| Cheilanthes tenuifolia | 41, 42 |
| Ajuga turkestania | 43, 76 |
| Dacrydium intermedium | 44, 65, 93, 94, 104 |
| Leuza carthamoides | 46 |
| Peniocreus greggy | 47 |
| Diploclisia glaucescens | 48 |
| Silene nutans | 49, 50, 101 |
| Ajuga repetans | 51, 52, 53, 54 |
| Laurencia pinnata | 55, 56, 57, 58, 59, 60, 61 |
| Polypodium aureum | 63, 105 |
| Pteridium aquilinum | 66, 71 |
| Silene praemixta | 68, 72, 85 |
| Pfafia iresinoides | 69, 97, 103 |
| Rhaponiticum charthamoides | 70, 98 |
| Echinops setifer | 73 |
| Wilcoxia viperina | 77 |
| Silene otites | 78, 80, 81, 86, 91, 92, 95, 96, 99, 100 |
| Geradia savaglia | 79 |
| Solanum xanthocarpum | 88 |
| Bombyx mori | 90 |
| Polyporus umbellatus FRIES | 111, 112, 113, 114, 115, 116, 117 |

As for the method for preparing the steroid derivative from the animal and plant origins described above, the steroid derivative can be easily obtained by using known methods including, for example, extraction and purification. Namely, a method is available in which an animal or plant origin is treated for extraction with a solvent or the like, and an objective steroid derivative is isolated and purified from an extract solution. The procedure for extraction may proceed in accordance with an ordinary process either at room temperature or with heating. The steroid derivative used in the present invention is extracted into a solvent by, for example, adding the solvent to the animal or plant origin described above, the solvent having a volume 2–20 times that of the animal or plant origin, and immersing it either for several hours in the case of being heated to a temperature in the vicinity of a boiling point, or for several days in the case of being left at room temperature. An extract thus obtained is purified by using, for example, liquid—liquid extraction, and chromatography with a carrier of ion exchange resin, porous powder such as silica gel, or a chemically modified material thereof. Thus the steroid derivative can be easily purified.

The solvent used for extraction is not specifically limited. However, a polar solvent is preferably used. Preferred solvents include, for example, water; alcohols such as ethanol and methanol; ethers such as diethyl ether and tetrahydrofuran; halogenated hydrocarbons such as chloroform and methylene chloride; ketones such as acetone and methyl ethyl ketone; and nitrites such as acetonitrile. These polar solvents may be used singly as one species or may be mixed with several species.

The steroid derivative thus obtained has an excellent blood flow amount-improving function and an excellent hair growth-facilitating function as shown in Examples described later.

(2) Cosmetic of the present invention

The cosmetic of the present invention is obtained by blending one or more species of the steroid derivatives represented by the general formula (1) or (2) described above as the blood flow amount-improving agent. The preferred blending amount varies depending on the type of the steroid derivative to be blended, however, it may be about 0.000001 to 10% by weight with respect to a total amount of the cosmetic.

The preferred blending amount is 0.000001 to 10% by weight with respect to a total amount of the cosmetic when the steroid derivative to be blended with the cosmetic is a compound having an excellent blood flow amount-improving function and an excellent hair growth-facilitating function even at an extremely low concentration. Such a steroid derivative among the steroid derivatives described above includes Paristerone, Ponasterone A, Inokosterone, Makisterone A, Makisterone C, 3-Epiecdysone, Cheilanthone B, 24(28)-Dehydromakisterone A, Integristerone A-22-O-α-D-galactopyranoside, 14α-Hydroxypinnasterol-2-acetate, Polypodosaponin A, Ponasteroside A, Pterosterone-24-O-β-D-glucopyranoside, Viticosterone E-22-O-benzoate, Deoxyecdysone-3-β-glucopyranoside, 2-Deoxyecdysone-25-O-β-glucopyranoside, 20-Hydroxyecdysone-3-O-α-galactopyranoside, and Polyporusterone A.

The preferred blending amount is 0.001 to 10% by weight with respect to a total amount of the cosmetic when the steroid derivative to be blended is a compound having an excellent blood flow amount-improving function and an excellent hair growth-facilitating function even at a relatively low concentration. Such a steroid derivative includes Ponasterone C, Takisterone, Makisterone B, Makisterone D, Pterosterone, Stachysterone C, Stachysterone D, Viticosterone E, Ajugasterone B, Ajugasterone C, Amarasterone A, Amarasterone B, Cyasterone, Isocyasterone, Epicyasterone, Capitasterone, Sengosterone, 26-Hydroxypolypodine B, 2-Deoxyecdysone, 3-Deoxyecdysone, 3-Dehydro-20-hydroxyecdysone, 3-Epi-20-hydroxyecdysone, Podecdysone B, Calonysterone, Carpesterol, Carthamosterone, Cheilanthone A, Cyasterone-22-acetate, Dacrysterone, 5-Deoxykaladasterone, Deoxyviperidone, 24-Epimakisterone A, Integristerone, 29-Norcyasterone, 29-Norcyasterone-2-acetate, 29-Norcyasterone-3-acetate, 29-Norsengosterone, Pinnasterol, Pinnasterol-2-acetate, 14α-Hydroxypinnasterol-3-acetate, 22-Epi-14α-hydroxypinnasterol-2-acetate, Podecdysone C, Ponasterone C-2-cinnamate, Praemiximisterone, Silenosterone, Stachysterone B, Turkesterone, Viperidone, Gerardiasterone, 2-Deoxyecdysone-3-acetate, 2-Deoxyecdysone-22-benzoate, 2-Deoxy-20-hydroxyecdysone, 20-Hydroxyecdysone-2-acetate, 20-Hydroxyecdysone-3, 22-O-α-D-digalactopyranosode, 20-Hydroxyecdysone-25-O-β-glucopyranoside, Podecdysone B-25-O-β-glucopyranoside, 20-Hydroxyecdysone and Polypodine B.

The preferred blending amount is 0.01 to 10% by weight with respect to a total amount of the cosmetic when the steroid derivative to be blended is, for example, Ponasterone B, Sidasterone A, Sidasterone B, Precyasterone, Kaladasterone, Abutasterone, Ajugalactone, Ajugasterone D, Osladin, 14α-Hydroxypinnasterol, Polypodine C, Poststerone, Rapisterone, Rubrosterone, Sogdysterone, Stachysterone A, 2-Deoxy-20-hydroxyecdysone-3-acetate, Sodium ecdysone-22-salfate, 3-Epi-2-deoxyecdysone, 14α-hydroxycarpesterol, 20-Hydroxy-5α-ecdysone, 20-Hydroxyecdysone-20-O-benzoate, 20-Hydroxyecdysone-22-O-benzoate, 20-Hydroxyecdysone-2-cinnamate, 20-Hydroxyecdysone-3-p-coumarate, 20-Hydroxyecdysone-2,3-acetonide, 20-Hydroxy-5α-ecdysone-22-O-benzoate, 20-Hydroxyecdysone-20,22-acetonide, Integristerone B, Muristerone A, Polypodine B-2-cinnamate, Polypodoaurein, Ecdysone, 2-Deoxy-20-hydroxyecdysone, 22-Acetoxy-20-hydroxyecdysone, Polyporusterone B, Polyporusterone C, Polyporusterone D, Polyporusterone E, Polyporusterone F, or Polyporusterone G.

Upon the use of each of the steroid derivatives described above to be contained in the cosmetic, if the blending amount is less than the minimum value in each of the preferable ranges of the blending amount, it is impossible to obtain a sufficient blood flow amount-improving function, and it is impossible to expect a hair-growing effect and a skin-beautifying effect so much. In any case, even if the steroid derivative is blended in an amount exceeding 10% by weight, the effect often becomes saturated, which is not economic.

The type or form of the agent of the cosmetic of the present invention is not specifically limited, which includes those ordinarily used as cosmetics including, for example, cosmetics for hair such as hair tonic, shampoo, rinse, pomade, hair lotion, hair cream, and hair treatment; cosmetics for skin such as lotion, emulsion, cream, aqueous gel, oil gel, ointment, under make-up, foundation, powder, lip stick, and eye liner; and agents for bath such as soft capsule, powder, granule, and liquid. These cosmetics can be produced in accordance with the same method as that for ordinary cosmetics except that the blood flow amount-improving agent of the present invention comprising the steroid derivative represented by the general formula (1) or (2) described above is blended.

The cosmetic of the present invention may be blended with those ordinary applied to cosmetics which may be appropriately selected, in addition to the blood flow amount-improving agent described above, from hydrocarbons such as liquid paraffin, vaseline, and squalane; esters such as isopropyl myristate (IPM), synthetic spermaceti, jojoba oil, and carnauba wax; animal and plant fats and oils such as olive oil and beef tallow; higher alcohols such as cetanol and stearyl alcohol; higher fatty acids such as stearic acid and oleic acid; surfactants including anionic surfactants such as sodium lauryl sulfate and alkylsulfosuccinic acid ester, cationic surfactants such as quaternary alkylamine salt, nonionic surfactants such as fatty acid monoglyceride and polyoxyethylene hardened castor oil, and amphoteric surfactants such as alkylbetaine; polyvalent alcohols such as glycerol and propylene glycol; lower alcohols such as ethanol and propanol; preservatives such as paraben and chlorhexidine gluconate; ultraviolet-absorbing agents such as paraaminobenzoic acid derivative and benzophenone derivative; antioxidants such as vitamin E and butylhydroxytoluene; thickeners such as gum arabic and carboxyvinylpolymer; humectants such as polyethylene glycol; pH adjusting agents such as citric acid salt and acetic acid salt; inorganic salts such as sodium sulfate and sodium carbonate; powders such as titanium oxide, silica gel, and talc; perfumes; dyes; and medicinal components in response to various objects such as hyaluronic acid, placenta extract, ginseng extract, and sterol glucoside.

The cosmetic of the present invention may be blended with components having blood flow amount improving functions, hair growth-facilitating components for the cosmetic for hair, and beautiful skin-forming components for the cosmetic for skin, in a range not to deteriorate the effect of the present invention, in addition to the steroid derivative represented by the general formula (1) or (2) as the blood flow amount-improving agent of the present invention.

BEST MODE FOR CARRYING OUT THE INVENTION

The present invention will be more specifically explained below with reference to Examples.

EXAMPLE 1

Blood Flow Amount-Improving Agent

The blood flow amount-improving agents of the present invention have been exemplified by the 117 species of the steroid derivatives shown in Table 1 described above. Among them, steroid derivatives of 112 species, except for Ecdysone (Steroid 106), 20-Hydroxyecdysone (Steroid 107), 2-Deoxy-20-hydroxyecdysone (Steroid 108), 22-Acetoxy-20-hydroxyecdysone (Steroid 109), and Polypodine B (Steroid 110) readily obtainable as commercially available products, were produced in accordance with the following method.

Methanol (10 L) was added to 1 kg (dry weight) of the animal or plant origin of each of the steroid derivatives shown in Table 2 described above, and soluble components were extracted by heating the contents under reflux for 2 hours with agitation. An obtained extract liquid is filtrated to remove insoluble matters, and then a filtrate was purified to isolate each of the steroid derivatives by using Diaion HP-20 column chromatography (produced by Mitsubishi Chemical, with an elution solvent of water: methanol=80:20→0:100), silica gel column chromatography (with an elution solvent of chloroform: methanol=100:0→0:100), and preparative high-performance liquid chromatography installed with an ODS column (acetonitrile: water=10:90→90:10). The yield for the 112 species of the obtained steroid derivatives is shown in Table 3.

TABLE 3

Yields of Various Steroid Derivatives
Obtained from 1 kg of Animal and Plant Origins

| Steroid No. | Yield (mg) | Steroid No. | Yield (mg) | Steroid No. | Yield (mg) |
|---|---|---|---|---|---|
| 1 | 550 | 39 | 25 | 77 | 5 |
| 2 | 2000 | 40 | 5 | 78 | 5 |
| 3 | 50 | 41 | 5 | 79 | 5 |
| 4 | 500 | 42 | 5 | 80 | 5 |
| 5 | 1500 | 43 | 5 | 81 | 5 |
| 6 | 120 | 44 | 10 | 82 | 5 |
| 7 | 10 | 45 | 5 | 83 | 5 |
| 8 | 3 | 46 | 10 | 84 | 5 |
| 9 | 2 | 47 | 15 | 85 | 5 |
| 10 | 4 | 48 | 15 | 86 | 5 |
| 11 | 15 | 49 | 20 | 87 | 5 |
| 12 | 10 | 50 | 15 | 88 | 5 |
| 13 | 5 | 51 | 15 | 89 | 5 |
| 14 | 5 | 52 | 10 | 90 | 5 |
| 15 | 25 | 53 | 10 | 91 | 5 |
| 16 | 10 | 54 | 5 | 92 | 5 |
| 17 | 45 | 55 | 5 | 93 | 5 |
| 18 | 25 | 56 | 2 | 94 | 5 |
| 19 | 5 | 57 | 3 | 95 | 5 |
| 20 | 5 | 58 | 5 | 96 | 5 |
| 21 | 5 | 59 | 5 | 97 | 5 |
| 22 | 5 | 60 | 5 | 98 | 5 |
| 23 | 5 | 61 | 5 | 99 | 5 |
| 24 | 5 | 62 | 5 | 100 | 5 |
| 25 | 15 | 63 | 5 | 101 | 5 |
| 26 | 45 | 64 | 5 | 102 | 5 |
| 27 | 45 | 65 | 15 | 103 | 5 |
| 28 | 50 | 66 | 10 | 104 | 10 |
| 29 | 40 | 67 | 5 | 105 | 5 |
| 30 | 20 | 68 | 5 | 111 | 3 |
| 31 | 30 | 69 | 5 | 112 | 3 |
| 32 | 20 | 70 | 5 | 113 | 0.3 |
| 33 | 60 | 71 | 5 | 114 | 0.1 |
| 34 | 35 | 72 | 5 | 115 | 0.2 |
| 35 | 15 | 73 | 5 | 116 | 0.1 |
| 36 | 3000 | 74 | 15 | 117 | 0.1 |
| 37 | 45 | 75 | 10 | | |
| 38 | 25 | 76 | 5 | | |

EXAMPLE 2

Test for Blood Flow Amount-Improving Function

The blood flow amount-improving function of the blood flow amount-improving agent of the present invention was evaluated by the following method by using the 112 species of the steroid derivatives obtained in Example 1 described above and commercially available products produced by Aldrich for Steroids 106 to 110.

The blood flow amount in vein at crop gland of a five weeks old hamster was observed under a microscope. After that, a sample (0.01 mL), which was obtained by solubilizing one species of the steroid derivatives described above to give a concentration of 0.005% by weight in an aqueous physiological saline solution of 0.05% by weight of polyoxyethylene (60) hardened castor oil, was directly administered dropwise to mucosa of the crop gland to investigate the influence on the blood flow amount. Tests were carried out in this manner for each of the 117 species of the steroid derivatives described above. A test for control was carried out in the same manner as described above except that only the aqueous physiological saline solution of 0.05% by weight of polyoxyethylene (60) hardened castor oil was used. It was confirmed that the control administration caused no change in the blood flow amount in vein at the hamster crop gland between before and after the administration.

After that, the degree of improvement in the blood flow amount after the administration as compared with that before the administration was evaluated for each of the steroid derivatives in accordance with the following evaluation standard. Results are shown in Table 4.

<Evaluation standard>

++: remarkably improved

+: improved

±: slightly improved

−: not improved

TABLE 4

Evaluation Results for Blood Flow Amount-
Improving Function of Steroid Derivatives

| Evaluation | Steroid No. |
|---|---|
| ++ | 1, 2, 9, 31, 42, 45, 59, 64, 66, 78, 82, 83, 96, 111 |
| + | 4, 5, 6, 7, 8, 10, 11, 12, 13, 14, 17, 18, 19, 20, 21, 22, 23, 24, 26, 27, 28, 29, 30, 32, 34, 35, 39, 40, 41, 43, 44, 46, 47, 48, 49, 50, 51, 52, 53, 54, 56, 58, 60, 61, 62, 65, 68, 69, 72, 75, 76, 77, 79, 80, 81, 84, 90, 95, 97, 103, 107 |
| ± | 3, 15, 16, 25, 33, 36, 37, 38, 55, 57, 63, 67, 70, 71, 73, 74, 85, 86, 87, 88, 89, 91, 92, 93, 94, 98, 99, 100, 101, 102, 104, 105, 106, 108, 109, 110, 112, 113, 114, 115, 116, 117 |

According to the results, it is clear that the blood flow amount-improving agent of the present invention has an excellent blood flow amount-improving function.

EXAMPLE 3

Test for Hair Growth-Facilitating Function

The hair growth-facilitating function and its concentration dependency of the blood flow amount-improving agent of the present invention were evaluated by the following method by using the 112 species of the steroid derivatives obtained in Example 1 described above and commercially available products (produced by Aldrich) for Steroids 106 to 110.

(1) Hair growth-facilitating functions of various steroid derivatives

Hairs were shaved on a portion of 2 cm square on the back of C3H mice which were 10 weeks old and grouped into 118 groups, each group comprising 5 mice. On the next day, a 0.03% by weight of ethanol solution of each of the steroid derivatives described above was applied in an amount of 0.03 mL to the shaved portion of each of the mice of 117 groups, while only ethanol was applied in the same amount to the shaved portion of each of the mice of one remaining group as control. After the application, the level of the hair growth degree was visually observed on the 14th day to evaluate the hair growth-facilitating function of each of the steroid derivatives by comparison with the control in accordance with the following standard.

<Evaluation standard>

++: remarkably fast hair growth as compared with mice in the control group

+: clearly fast hair growth as compared with mice in the control group

±: slightly fast hair growth as compared with mice in the control group
−: same hair growth as that of mice in the control group

TABLE 5

Evaluation Results for Hair Growth-Facilitating Function of Steroid Derivatives

| Evaluation | Steroid No. |
|---|---|
| ++ | 2, 5, 7, 9, 31, 45, 49, 59, 64, 66, 69, 78, 82, 96, 111 |
| + | 1, 4, 6, 8, 10, 11, 12, 13, 14, 17, 18, 19, 20, 21, 22, 23, 24, 26, 27, 28, 29, 30, 32, 34, 35, 39, 40, 41, 42, 43, 44, 46, 47, 48, 50, 51, 52, 54, 56, 58, 60, 61, 62, 65, 68, 72, 75, 76, 77, 79, 83, 95, 96, 97, 103, 107, 110 |
| ± | 3, 15, 16, 25, 33, 36, 37, 38, 53, 55, 57, 63, 67, 70, 71, 73, 74, 80, 81, 84, 85, 86, 87, 88, 89, 90, 91, 92, 93, 94, 98, 99, 100, 101, 102, 104, 105, 106, 108, 109, 112, 113, 114, 115, 116, 117 |

According to the results, it is clear that the blood flow amount-improving agent of the present invention has an excellent hair growth-facilitating function.

(2) Concentratiion dependency of hair growth-facilitating function

An experiment for evaluating the hair growth-facilitating function was carried out in the same manner as the item (1) described above, but the steroid derivative concentration was varied to give various concentrations as shown in table 6 by using Ponasterone A (Steroid 2), Ponasteroside A (Steroid 66), 20-Hydroxyecdysone (Steroid 107), Polyporusterone A (Steroid 111), and Polyporusterone B (Steroid 112) selected from the steroid derivatives as the blood flow amount-improving agent of the present invention. Results are shown in Table 6.

TABLE 6

Evaluation Results for Concentration Dependency of Hair Growth-facilitating Function of Steroid Derivatives

| Concentration in ethanol solution of steroid derivative [% by weight] | Evaluation Steroid No. | | | | |
|---|---|---|---|---|---|
| | 2 | 66 | 107 | 111 | 112 |
| 0.000003 | − | ± | − | ± | − |
| 0.00003 | ± | + | − | + | − |
| 0.0003 | ± | + | − | ++ | − |
| 0.003 | + | ++ | ± | ++ | ± |
| 0.03 | ++ | ++ | + | ++ | ± |
| 0.3 | ++ | ++ | + | ++ | + |
| 1.0 | ++ | ++ | ++ | ++ | ++ |

According to the results, it has been found that the blood flow amount-improving agent of the present invention can exhibit an excellent hair growth-facilitating function even at an extremely low concentration.

EXAMPLE 4

Percutaneous Stimulation Test (Local Toxicity Test)

The following percutaneous stimulation test was carried out for the blood flow amount-improving agent of the present invention to evaluate safety by using the 112 species of the steroid derivatives obtained in Example 1 described above and commercially available products (produced by Aldrich) for Steroids 106 to 110.

Hairs were shaved on a portion of 3 cm square on the back of white type guinea pigs of Hartley line which were grouped into 117 groups, each group comprising 3 guinea pigs. A hydrophilic ointment containing 10% by weight of each of the steroid derivatives described above was continuously administered to the shaved portion once a day in an amount of 0.05 mL for each administration over 5 days. On the 6th day after the start of administration, the percutaneous stimulation was evaluated in accordance with a patch test standard in Japan (Dermatology Society of Japan) shown below.

<Patch test standard in Japan>

−: no reaction

±: false positive reaction

+: positive reaction

++: reaction accompanied with edema

As a result, all of the guinea pigs exhibited "no reaction". According to this fact, it is understood that the steroid derivatives described above to be used as the blood flow amount-improving agent of the present invention are excellent in percutaneous safety.

EXAMPLE 5

Acute Toxicity Test

The acute toxicity test was carried out for the blood flow amount-improving agent of the present invention to evaluate safety by using the 112 species of the steroid derivatives obtained in Example 1 described above and commercially available products (produced by Aldrich) for Steroids 106 to 110.

Each of the steroid derivatives described above was administered orally in an amount of 1 g/kg to ICR mice (male, body weight: 25 to 35 g) which were 5 weeks old and grouped into 117 groups respectively, each group comprising 6 mice. On the 14th day after the administration, it was judged whether they were alive or dead, and $LD_{50}$ values were determined.

As a result, no case of death was observed in the mice of all groups. Therefore, it is assumed that the $LD_{50}$ value is not less than 1 g/kg. Thus it is understood that the steroid derivatives described above to be used as the blood flow amount-improving agent of the present invention have high safety.

Next, Examples of cosmetics will be explained, in which each of the steroid derivatives obtained in Example 1 described above and commercially available products (produced by Aldrich) for Steroids 106 to 110 are blended as the blood flow amount-improving agent of the present invention. Blending amounts referred to below are all represented by parts by weight.

EXAMPLES 6 TO 8

Hair Lotion

Components for formulation shown in Table 7 were weighed, mixed and solubilized by agitation at room temperature to obtain hair lotions.

TABLE 7

Compositions of Hair Lotions of Examples 6 to 8

| Component | Blending amount (parts by weight) | | |
|---|---|---|---|
| | Example 6 | Example 7 | Example 8 |
| Paristerone (Steroid 1) | 9.0 | — | — |
| Ecdysone (Steroid 106) | — | 9.0 | — |
| Polyporusterone A (Steroid 111) | — | — | 9.0 |
| Menthol | 0.2 | 0.2 | 0.2 |
| Propylene glycol | 5.0 | 5.0 | 5.0 |
| Vitamin E | 0.1 | 0.1 | 0.1 |
| Diphenhydramine hydrochloride | 0.1 | 0.1 | 0.1 |
| Dipotassium glycyrrhetinate | 0.1 | 0.1 | 0.1 |
| Methylparaben | 0.2 | 0.2 | 0.2 |
| Ethanol | 50.0 | 50.0 | 50.0 |
| Perfume | 1.0 | 1.0 | 1.0 |
| Purified water | 34.3 | 34.3 | 34.3 |

EXAMPLE 9 TO 11

Hair Tonic

Components for formulation shown in Table 8 were weighed, mixed and solubilized by agitation at room temperature to obtain hair tonics.

TABLE 8

Compositions of Hair Tonics of Examples 9 to 11

| Component | Blending amount (parts by weight) | | |
|---|---|---|---|
| | Example 9 | Example 10 | Example 11 |
| Ponasterone A (Steroid 2) | 0.3 | — | — |
| 20-Hydroxyecdysone (Steroid 107) | — | 0.3 | — |
| Polyporusterone B (Steroid 112) | — | — | 0.3 |
| Vitamin E | 0.2 | 0.2 | 0.2 |
| Capsicum tincture | 0.1 | 0.1 | 0.1 |
| Ethanol | 50.0 | 50.0 | 50.0 |
| Propylene glycol | 5.0 | 5.0 | 5.0 |
| Vitamin $B_2$ | 0.1 | 0.1 | 0.1 |
| Diphenhydramine hydrochloride | 0.1 | 0.1 | 0.1 |
| Placenta extract | 0.1 | 0.1 | 0.1 |
| Benzalkonium chloride | 0.1 | 0.1 | 0.1 |
| Perfume | 0.5 | 0.5 | 0.5 |
| Purified water | 43.5 | 43.5 | 43.5 |

EXAMPLES 12 TO 14

Cream

Components A and components B shown in Table 9 were separately heated and dissolved at 80° C. After that, the components B were gradually added to the components A with agitation, to which a component C was added, followed by cooling to obtain creams.

TABLE 9

Compositions of Creams of Examples 12 to 14

| Component | Blending amount (parts by weight) | | |
|---|---|---|---|
| | Example 12 | Example 13 | Example 14 |
| Component A | | | |
| Vaseline | 7.0 | 7.0 | 7.0 |
| Bead wax | 8.0 | 8.0 | 8.0 |
| Liquid paraffin | 37.0 | 37.0 | 37.0 |
| POE (20) behenyl ether | 3.0 | 3.0 | 3.0 |
| Glyceryl monostearate | 2.0 | 2.0 | 2.0 |
| Component B | | | |
| Ponasterone B (Steroid 3) | 0.03 | — | — |
| 22-Acetoxy-20-hydroxyecdysone (Steroid 109) | — | 0.03 | — |
| Polyporusterone A (Steroid 111) | — | — | 0.03 |
| Propylene glycol | 5.0 | 5.0 | 5.0 |
| Diphenhydramine hydrochloride | 0.1 | 0.1 | 0.1 |
| Dipotassium glycyrrhetinate | 0.12 | 0.12 | 0.12 |
| Chlorhexidine gluconate | 0.05 | 0.05 | 0.05 |
| Purified water | 42.6 | 42.6 | 42.6 |
| Component C | 0.1 | 0.1 | 0.1 |
| Perfume | | | |

EXAMPLES 15 TO 17

Hair Treatment

Components A and components B shown in Table 10 were separately heated and dissolved at 80° C. respectively. The components B were gradually added to the components A with agitation, to which a component C was added, followed by cooling to obtain hair treatments.

TABLE 10

Compositions of Hair Treatments of Examples 15 to 17

| Component | Blending amount (parts by weight) | | |
|---|---|---|---|
| | Example 15 | Example 16 | Example 17 |
| Component A | | | |
| Liquid paraffin | 2.0 | 2.0 | 2.0 |
| Methylpolysiloxane (10 c.s.) | 2.0 | 2.0 | 2.0 |
| Behenyl alcohol | 4.0 | 4.0 | 4.0 |
| Component B | | | |
| Ponasterone C (Steroid 4) | 0.5 | — | — |
| Inokosterone (Steroid 5) | 0.5 | — | — |
| 2-Deoxy-20-hydroxyecdysone (Steroid 108) | — | 1.0 | — |
| Polyporusterone B (Steroid 112) | — | — | 1.0 |
| Stearyltrimethyl ammonium chloride | 3.5 | 3.5 | 3.5 |
| Propylene glycol | 5.0 | 5.0 | 5.0 |
| Purified water | 82.0 | 82.0 | 82.0 |
| Component C | 0.5 | 0.5 | 0.5 |
| Perfume | | | |

EXAMPLE 18 TO 20

Shampoo

Components for formulation shown in Table 11 were weighed, mixed, heated and dissolved at 80° C., followed by cooling to obtain shampoos.

TABLE 11

Compositions of Shampoos of Examples 18 to 20

| Component | Blending amount (parts by weight) | | |
|---|---|---|---|
| | Example 18 | Example 19 | Example 20 |
| Lauryl sulfate triethanolamine | 15.0 | 15.0 | 15.0 |
| Coconut oil fatty acid diethanol amide | 2.0 | 2.0 | 2.0 |
| Propylene glycol | 5.0 | 5.0 | 5.0 |
| Takisterone (Steroid 6) | 3.0 | — | — |
| Makisterone A (Steroid 7) | 2.0 | — | — |
| Polypodine B (Steroid 110) | — | 5.0 | — |
| Polyporusterone A (Steroid 111) | — | — | 5.0 |
| Purified water | 72.5 | 72.5 | 72.5 |
| Perfume | 0.5 | 0.5 | 0.5 |

EXAMPLES 21 TO 31

Hair Tonic

Components for formulation shown in Table 12 were weighed, mixed, and dissolved by agitation at room temperature to obtain hair tonics.

TABLE 12

Compositions of Hair Tonics of Examples 21 to 31

| Component (Steroid No. herein shown in parentheses) | Blending amount (parts by weight) | | | | | | | | | | |
|---|---|---|---|---|---|---|---|---|---|---|---|
| | 21 | 22 | 23 | 24 | 25 | 26 | 27 | 28 | 29 | 30 | 31 |
| Makisterone D (10) | 0.05 | — | — | — | — | — | — | — | — | — | — |
| Viticosterone E (14) | — | 0.05 | — | — | — | — | — | — | — | — | — |
| Viperidone (77) | — | — | 0.05 | — | — | — | — | — | — | — | — |
| 22-Epi-14α-hydroxy-pinnasterol-2-acetate (61) | — | — | — | 0.05 | — | — | — | — | — | — | — |
| Precyasterone (25) | — | — | — | — | 0.05 | — | — | — | — | — | — |
| Rubrosterone (71) | — | — | — | — | — | 0.05 | — | — | — | — | — |
| Polypodine C (63) | — | — | — | — | — | — | 0.05 | — | — | — | — |
| Podecdysone B (34) | — | — | — | — | — | — | — | 0.05 | — | — | — |
| Calonysterone (35) | — | — | — | — | — | — | — | — | 0.05 | — | — |
| Abutasterone (36) | — | — | — | — | — | — | — | — | — | 0.05 | — |
| Epicyasterone (23) | — | — | — | — | — | — | — | — | — | — | 0.02 |
| Capitasterone (24) | — | — | — | — | — | — | — | — | — | — | 0.03 |
| Tocopherol | 0.20 | 0.20 | 0.20 | 0.20 | 0.20 | 0.20 | 0.20 | 0.20 | 0.20 | 0.20 | 0.20 |
| Capsicum tincture | 0.10 | 0.10 | 0.10 | 0.10 | 0.10 | 0.10 | 0.10 | 0.10 | 0.10 | 0.10 | 0.10 |
| Propylene glycol | 5.00 | 5.00 | 5.00 | 5.00 | 5.00 | 5.00 | 5.00 | 5.00 | 5.00 | 5.00 | 5.00 |
| Minoxidil | 0.10 | 0.10 | 0.10 | 0.10 | 0.10 | 0.10 | 0.10 | 0.10 | 0.10 | 0.10 | 0.10 |
| Ethanol | 50.00 | 50.00 | 50.00 | 50.00 | 50.00 | 50.00 | 50.00 | 50.00 | 50.00 | 50.00 | 50.00 |
| Lavender essence | 0.10 | 0.10 | 0.10 | 0.10 | 0.10 | 0.10 | 0.10 | 0.10 | 0.10 | 0.10 | 0.10 |
| Perfume | 0.50 | 0.50 | 0.50 | 0.50 | 0.50 | 0.50 | 0.50 | 0.50 | 0.50 | 0.50 | 0.50 |
| Purified water | 43.95 | 43.95 | 43.95 | 43.95 | 43.95 | 43.95 | 43.95 | 43.95 | 43.95 | 43.95 | 43.95 |

EXAMPLE 32 TO 35

Hair Lotion

Components for formulation shown in Table 13 were weighed, mixed, and dissolved by agitation at room temperature to obtain hair lotions. A hair lotion of Comparative Example was produced in the same manner except that it contained no blood flow amount-improving agent of the present invention.

TABLE 13

Compositions of Hair lotions of Examples 32 to 35 and Comparative Example 1

| Component | Blending amount (parts by weight) | | | | |
|---|---|---|---|---|---|
| | Example | | | | Comp. Ex. |
| | 32 | 33 | 34 | 35 | 1 |
| Ecdysone (Steroid 106) | 0.3 | 0.03 | — | — | — |
| Polyporusterone A (Steroid 111) | — | — | 0.0003 | 0.00003 | — |
| Menthol | 0.2 | 0.2 | 0.2 | 0.2 | 0.2 |
| Propylene glycol | 5.0 | 5.0 | 5.0 | 5.0 | 5.0 |
| Vitamin E | 0.1 | 0.1 | 0.1 | 0.1 | 0.1 |
| Diphenhydramine hydrochloride | 0.1 | 0.1 | 0.1 | 0.1 | 0.1 |
| Dipotassium glycyrrhetinate | 0.1 | 0.1 | 0.1 | 0.1 | 0.1 |
| Methylparaben | 2.0 | 2.0 | 2.0 | 2.0 | 2.0 |
| Ethanol | 50.0 | 50.0 | 50.0 | 50.0 | 50.0 |
| Perfume | 1.0 | 1.0 | 1.0 | 1.0 | 1.0 |
| Purified water | 43.0 | 43.27 | 43.2997 | 43.29997 | 43.3 |

EXAMPLE 36

Evaluation for Hair Growth-Facilitating Function of Cosmetics for Hair

A test for actual use was carried out in relation to the hair growth-facilitating function by using the hair lotions of Examples 33, 34 and Comparative Example 1 described above.

Sixty male panelers, who were 36 to 54 years old and suffered from baldness and thin hair, were divided into 3 groups, each group comprising 20 panelers. The first group panelers used the hair lotion obtained in Example 33, the second group panelers used the hair lotion obtained in Example 34, and the third group paneler used the hair lotion in Comparative Example 1. All panelers continuously used their hair lotions twice a day over 60 days. The degree of improvement in baldness and thin hair was judged visually. Results are shown in Table 14.

TABLE 14

Results of Evaluating for
Hair Growth-Facilitating Function of Cosmetics for Hair

| Evaluation standard | Number of people (individuals) | | |
|---|---|---|---|
| | Example 33 | Example 34 | Com. Ex. 1 |
| Remarkably improved | 2 | 8 | 0 |
| Improved | 11 | 12 | 5 |
| Unchanged | 7 | 0 | 15 |
| Deteriorated | 0 | 0 | 0 |

According to the results, it is understood that the cosmetic for hair of the present invention clearly has an excellent improving function for baldness and thin hair as compared with the cosmetic for hair containing no blood flow amount-improving agent of the present invention.

Industrial Applicability

The blood flow amount-improving agent of the present invention has an excellent blood amount-improving function, and it is highly safe. The cosmetic of the present invention contains the blood flow amount-improving agent. Thus the cosmetic for hair is excellent in the hair-growing effect, and the cosmetic for skin is excellent in the skin-beautifying effect. In addition, the cosmetic of the present invention can be continuously used safely over a long period.

What is claimed is:

1. A hair growth enhancing cosmetic comprising polyporusterone A of the following formula in an amount of 0.000001% to 10% by weight to enhance hair growth, and a cosmetically acceptable carrier:

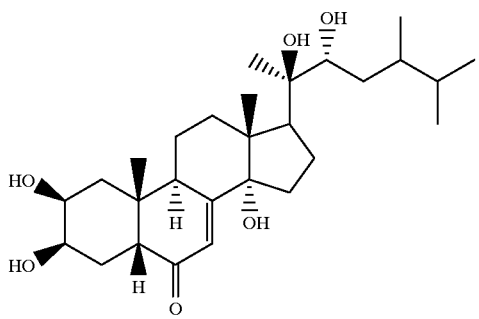

2. A method for enhancing hair growth comprising administering to hair and/or scalp a hair growth enhancing cosmetic including polyporusterone A of the following formula in an amount effective to enhance hair growth in a cosmetically acceptable carrier:

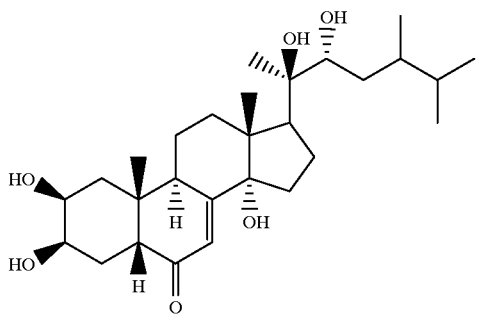

3. The method for enhancing hair growth according to claim 2, wherein polyporusterone A is administered in the form of a composition including in an amount of 0.000001% to 10% by weight.

* * * * *